United States Patent [19]
Purcell

[11] Patent Number: 5,837,728
[45] Date of Patent: Nov. 17, 1998

[54] 9-CIS RETINOIC ACID ESTERS AND AMIDES AND USES THEREOF

[75] Inventor: William P. Purcell, Memphis, Tenn.

[73] Assignee: Molecular Design International, Memphis, Tenn.

[21] Appl. No.: 380,011

[22] Filed: Jan. 27, 1995

[51] Int. Cl.$^6$ .................................................. A62K 31/215
[52] U.S. Cl. .......................... 514/529; 514/559; 554/221
[58] Field of Search ............................ 554/221; 514/559, 514/529

[56] References Cited

U.S. PATENT DOCUMENTS

| | | | |
|---|---|---|---|
| 4,523,042 | 6/1985 | Loev et al. ................................. | 568/824 |
| 5,124,356 | 6/1992 | Purcell et al. ........................... | 514/529 |

FOREIGN PATENT DOCUMENTS 2096196  11/1993  Canada .......................... A61K 31/59

*Primary Examiner*—Gary Geist
*Attorney, Agent, or Firm*—James S. Waldron

[57] ABSTRACT

Esters and amides of 9-cis-retinoic acid are synthesized, formulated into pharmaceutically acceptable carriers and administered for the treatment of acne vulgaris, cystic acne, hyper-pigmentation, hypo-pigmentation, psoriasis, dermal and epidermal hypoplasia and kerotoses, the reduction of wrinkling of the skin as an incident of aging and actinic damage, normalization of the production of sebum, the reduction of enlarged pores, promoting the rate of wound healing, limiting of scar tissue formation during healing and the like. They are additionally useful for treatment or amelioration of the same additional classes of skin disorders as is retinoic acid itself and other retinoids. These disorders include ichthyoses (e.g., ichthyosis hystrix, epidermolytic hyperkeratosis, and lamellar ichthyosis), follicular disorders (e.g., pseudofolliculites, senile comedones, nevus comidonicas, and trichostatis spinulosa), benign epithelial tumors (e.g., flat warts, trichoepithelioma, and molluscum contagiosum), perforated dematoses (e.g., elastosis perforans seripiginosa and Kyrles disease), and disorders of keratinization (e.g., Dariers disease, keratoderma, hyperkeratosis plantaris, pityriasis rubra pilaris, lichen planus acanthosis nigricans, and psoriasis). The esters and amides of 9-cis-retinoic acid are also effective for the non-irritating treatment of effects attributable to aging and particularly to photodamage and photoaging. The use of these compounds extends to non-irritating treatments involving the retardation and reversal of additional dermal and cosmetic conditions which are ameliorated by tretinoin such as the effacement of wrinkles, improvement in appearance, namely color and condition of the skin, spots caused from exposure to the sun as well as other skin disorders. The esters and amides of 9-cis-retinoic acid are exceptionally active when compared to other retinoids employed for such indications, and are also exceptionally safe in effective therapeutic doses in contrast to other retinoids.

40 Claims, No Drawings

9-CIS RETINOIC ACID ESTERS AND AMIDES AND USES THEREOF

BACKGROUND OF THE INVENTION

TECHNICAL FIELD

The present invention relates to the field of 9-cis retinoic acid and its esters and amides, and particularly to their uses for a variety of therapeutic and prophylactic treatments of the skin. The present invention particularly relates to 9-cis-retinoic acid esters which are effective in the treatment of acne and other skin disorders when administered either topically or orally and which show few if any side effects.

RELATED CASES

The inventor of the present invention is one of the inventors of prior U.S. Pat. Nos. 4,677,120; 4,885,311; 4,994,491; 5,049,584; 5,124,356; and Re. 34,075.

STATE OF THE ART

A number of dermal uses have been developed for a wide diversity of retinoids, including retinol (Vitamin A), retinal, all-trans-retinoic acid, and 13-cis-retinoic acid, as well as a variety of esters and similar derivatives.

Vitamin A has long been employed for dermal treatments, particularly for the treatment of acne in a variety of its manifestations. The use of Vitamin A itself has been limited because of the toxic character of the compound when administered in excess.

Vitamin A esters, such as Vitamin A palmitate, for example, are considered safer, although these materials too have substantial levels of toxicity that limits the concentrations at which the compounds can be administered.

β-Carotene, as a Vitamin A precursor has also been explored, with the expectation of greater safety. The precursor is less effective, however, since it is itself largely inactive and must be cleaved to the active Vitamin form before the desired effects are produced, and the cleavage is difficult to manage, predict and control.

Retinal has not achieved any significant acceptance for dermal uses because of the instability of the compound under exposure to heat, oxygen and ultraviolet light. The instability of the compound is unacceptable for most candidate uses.

All-trans-retinoic acid is, to date, the most commonly used dermal retinoid, in topical form (RETIN A®, Ortho Pharmaceuticals, Inc., a subsidiary of Johnson & Johnson). It has been approved for use in the treatment of acne vulgaris and related forms of acne. A substantial level of administration for other indications has not yet been approved, including anti-wrinkling and antiactinic treatments of the skin. All-trans-retinoic acid has been demonstrated to be irritating to the skin, producing inflammation in a substantial proportion of users.

In severe cases of cystic acne, oral doses of 13-cis retinoic acid have proved quite effective (ACCUTANE®, Roche Dermatologics, a Division of Hoffmann-LaRoche Inc.). The compound is, however, highly teratogenic and mutagenic, and is strictly contraindicated in women of child-bearing potential.

A number of retinoids have been identified with antiaging and antiactinic properties, including esters and amides of 13-cis-retinoic acid and all-trans-retinoic acid. In many cases these compounds have activities comparable to the parent acid and comparable inflammatory and irritating characteristics, although some are known to be safer and less irritating than others (sometimes at the expense of reduced effectiveness).

Such retinoids have also been shown to be of benefit in the reduction of skin cancers and precancerous lesions of the skin, although to date use for such indications have not been approved by regulatory authorities.

Retinol (vitamin A) and retinoic acid (vitamin A acid), its isomers, and certain of its analogs are known to have beneficial effects in the treatment of acne and keratinizing skin disorders.

Acne affects large patient populations and is a common inflammatory skin disorder which usually localizes on the face. Fortunately, the disease usually disappears and in the interval of months or years between onset and resolution, therapy, although not curative, can satisfactorily suppress the disease in the majority of patients.

A small number of acne patients with severe disease show little or no response to intensive therapeutic efforts including the use of high doses of oral tetracycline, dapsone, prednisone, and, in women, estrogen. In many cases, these drugs afford only a modest degree of control while the side effects of these agents severely restrict their usefulness. Patients with nodulocystic acne suffer from large, inflammatory, suppurative nodules appearing on the face, and frequently the back and chest. In addition to their appearance, the lesions are tender and often purulently exudative and hemorrhagic. Disfiguring scars are frequently inevitable.

Therapies for acne involve local and systemic administration of vitamin compounds, collectively know as retinoids. Topical application of all-trans-retinoic acid has been tried with some success, particularly against comedones or blackheads, but this condition frequently returns when the treatment is withdrawn. (All-trans-retinoic acid is also known as tretinoin. These terms are used interchangeably throughout this specification.) Additionally, retinoic acid applied topically can be highly irritating and its use can be painful for the patient depending on the concentration used and the frequency of application.

A number of side effects complicates the administration of large doses of vitamin A. Among the many symptoms of hypervitaminosis A are weight loss, desquamation of the skin, hair loss, irritation of the oral and pharyngeal mucosa, and nose bleeds, headaches, bone pain, liver toxicity due to storage of vitamin A in the liver, papilledena, pseudotumor cerebri, demineralization, and periosteal thickening of the bones. Because of these and other side effects of oral treatment with vitamin A and all-trans-retinoic acid, which produces similar side effects, they are rarely recommended for dermatopathic conditions.

Chronic sun exposure has been determined to create a number of skin disorders including skin cancer which is usually discernible by the presence of lesions known as keratoses as well as photoaging (or dermatoheliosis) of the skin which is characterized by wrinkling, sallowness, roughness and mottled pigmentation. In an article entitled, Topical Tretinoin Improves Photoaged Skin, JAMA 259, vol. 4, pgs. 527–532, Jan. 22/29, 1988, the authors Webb et al. report that photoaging of the skin of middle-aged and elderly Caucasians could be improved within a 16-week period by daily topical application of a cream containing 0.1% tretinoin (all-trans-retinoic acid).

A side effect which complicates the administration of tretinoin, is that the therapy is irritating to the skin and induces dermatitis of several weeks duration in almost all of the subjects undergoing the tretinoin therapy. Redness, peeling, stinging, burning and dryness were consistently experienced by nearly all subjects. Eleven of fifteen subjects experienced dermatitis severe enough to require the use of topical steroids to control the dermatitis. Three of fifteen withdrew from the tretinoin therapy due to the severity of the tretinoin-induced dermatitis. Also effects on the histology of the epidermal and stratum corneum layers of the dorsal forearm skin were noted in the tretinoin treated areas. Because of these side effects, recommendation for use of the therapy is inhibited and is not used to full advantage. A method of dermal therapy that would retain the effectiveness of tretinoin but which would be essentially non-irritating would provide a much needed solution to the treatment of photoaging. Further, non-irritating effective treatment of other skin disorder such as skin cancer would meet a long felt need in dermal therapy.

The Handbook of Nonprescription Drugs, 5$^{th}$ ed., 1977, A.P.A. pub., pp. 140, 319, 320, discloses the use of vitamin A and retinoic acid in the treatment of acne (unspecified). However, the disclosure of this publication is opposite to that of the subject invention, in that it states, The systemic use of vitamin A for the treatment of acne, . . . is not warranted by clinical evidence at p. 140; and that, Treatments that have been abandoned or have not been proved effective include oral vitamin A at p. 320.

J. V. Straumford reported a systemic usage of large oral doses of retinol, the alcohol form of vitamin A, over a long period of time for the treatment of acne. (Straumford, J. V., Vitamin A: Its Effect on Acne, Northwest Med., 42: 219–255, August, 1943). These results, however, have been disputed and systemic therapy of acne utilizing retinol has been challenged by other investigators. (Anderson, J. A. D., et al., Vitamin A in Acne Vulgaris, Brit. Med. J., 2:294–296, August, 1963; Lynch, F. W., et al., Acne Vulgaris Treated with Vitamin A, Arch. Derm. 55:355, 357, March, 1947; and Mitchell, G. H., et al., Results of Treatment of Acne Vulgaris by Intramuscular Injections of Vitamin A, Arch. Derm. 64:428–434. October, 1951.)

Topical administration of retinoic acid for the treatment of acne was reported by Kligman, et al., (Arch. Derm. 99:469–476, 1969, U.S. Pat. No. 3,729,568). The effectiveness of this treatment as disclosed by Kligman is often associated with a noticeable irritating effect of topically applied retinoic acid.

Esters and amides of trans-retinoic acid which are useful for the treatment of acne are claimed in U.S. Pat. No. 4,055,659 (all-trans-retinoyloxyacetamide), U.S. Pat. No. 4,126,697 (4-(all-trans-retinoyloxyacetyl)-catechol), U.S. Pat. No. 4,126,698 (2-hydroxyethyl all-trans-retinoate), and U.S. Pat. No. 4,304,787 (benzyl all-trans-retinoate). All four of these patents to Gander, et al. also disclose mixed 2-hydroxy-1-propyl and 1-hydroxy-2-propyl all-trans-retinoates, N-(3,4-methylene-dioxyphenyl methyl) all-trans-retinamide, and 4-nitrobenzyl all-trans-retinoate. The effectiveness of all these compounds was shown through testing which measured increase in DNA synthesis in epidermal cells. This ability has been associated with the effectiveness of retinoic acid in the treatment of acne. See, for example, Christophers and Braun-Falco, Stimulation of Epidermal DNA-Synthesis with Vitamin A-Acid, Arch. Klin. Exp. Derm. 232: 427–433 (1968) and Wolfe, et al., Changes in Epidermal Differentiation After Vitamin A Acid, Arch. Klin. Exp. Derm. 237: 744–795 (1970). No claim is made and no testing is disclosed in the Gander, et al. patents which indicates that the esters or amides show fewer or greater side effects than trans-retinoic acid.

The process for treating acne vulgaris topically utilizing retinal, the aldehyde form of vitamin A, is disclosed in U.S. Pat. No. 3,932,665. The aldehyde form, unlike the acid form of vitamin A, exerts its therapeutic effect without producing irritation, inflammation, erythema, or peeling of the skin. This patent also discloses the topical use of 13-cis-retinal in the treatment of acne vulgaris.

The method of treating acne with C-20 and C-22 vinylogs of desmethyl retinoic acid is disclosed in U.S. Pat. No. 3,882,244. These vinylogs as disclosed in the patent are applied topically to the site of the acne infection as a solution, ointment, or powder. The treatment of acne vulgaris with retinoic acid analogs, particularly 11-(2,6,6-trimethylcyclohex-1-enyl-1)-5,9-dimethylundeca-2,4,6,8,10-pentenoic acid is disclosed in U.S. Pat. No. 3,934,028. This compound can be used either internally or topically. When taken orally, the daily dosage of this compound ranged from 30–300 mg taken over from 2 to 8 weeks. However, there is no indication that the compound leads to remission from the disease after administration of the compound is withdrawn.

Other drugs presently used in the treatment of acne include benzoyl peroxide, tretinoin (all-trans-retinoic acid, Retin-A Ortho), clindamycin, tetracyline, erythromycin, minocycline, and estrogens (for females).

Benzoyl peroxide is considered safe and effective in mild and moderate acne treatment. Tretinoin is effective but has the previously mentioned deleterious side effects, as well as accelerating photocarcinogenesis. The antibiotics are reasonably effective but have side effects such as gastrointestinal problems including reports of pseudomembranous colitis. Estrogens are sometimes effective in treating acne, but the side effects of these drugs make them less than desirable.

The use of 13-cis-retinoic acid derivatives for the treatment of acne and other skin diseases is disclosed in U.S. Pat. No. 4,677,120 of Parish et al. All-trans analogs are disclosed in U.S. Pat. No. 4,885,311. The derivatives are claimed for use in either oral or topical treatment of the disease. These derivatives have been found to minimize the toxic side-effects associated with the use of all-trans and 13-cis-retinoic acid in the treatment of acne.

See also the following prior art cited in the record of our additional related prior U.S. Pat. Nos. 4,677,120, 4,885,311, 4,994,491; 5,049,584; 5,124,356; and Re. 34,075:

| U.S. PATENT DOCUMENTS | | | |
|---|---|---|---|
| 2,424,994 | 8/1947 | Milas | 260-410.9V |
| 2,576,103 | 11/1951 | Cawley et al. | 260-410.9V |
| 2,917,523 | 12/1959 | Pommer et al. | 260-410.9V |
| 2,951,853 | 9/1960 | Matsui | 260-410.9V |
| 3,287,382 | 11/1966 | van Leeuwen | 260/410.9V |
| 3,928,400 | 12/1975 | Olson et al. | 260/410.9V |
| 3,931,257 | 01/1976 | Pawson | 260/408 |
| 3,984,544 | 10/1976 | Casmer et al. | 514-177 |
| 4,055,659 | 10/1977 | Gander et al. | 514-552 |
| 4,108,880 | 8/1978 | Gander et al. | 260-410 |
| 4,190,594 | 2/1980 | Gander et al. | 260-404 |
| 4,216,224 | 8/1980 | Yu et al. | 514-561 |
| 4,529,600 | 7/1985 | Dawson et al. | 514-529 |
| 4,677,120 | 6/1987 | Parish et al. | 514-549 |
| 4,877,805 | 10/1989 | Kligman | 514-381 |
| 4,885,311 | 12/1989 | Kligman | 514/549 |
| 4,888,342 | 12/1989 | Kligman | 514/419 |
| NON-U.S. PATENT DOCUMENTS | | | |
| 106926 | 5/1984 | | EP |
| 2050658 | 5/1972 | | DE |
| 2081478 | 12/1971 | | FR |

PROBLEMS IN THE ART

In general terms, there is a balancing of safety related issues against effectiveness of the retinoids. The most common indications for retinoids are not related to mortality or severe morbidity issues. Acne vulgaris, wrinkles and skin photo-damage are largely cosmetic concerns. While the psychodynamics of such conditions and their effective treatment can be quite compelling, significant risks of side effects are not justifiable and safer and more effective modalities of treatment are needed. Other indications for the use of retinoids in dermal therapeutic indications are more significant, and higher levels of adverse side effects are more justifiable, but even in those contexts, greater safety is needed.

While a vast array of modifications of the existing compounds have been investigated, there is a considerable need to provide greater safety at the existing levels of effectiveness or greater levels of effectiveness at the existing level of safety. It would, of course, be most beneficial to increase both safety and effectiveness of the retinoids.

OBJECTS OF THE INVENTION

It is an object of the present invention to provide novel esters and amides of 9-cis-retinoic acid.

It is another object of the present invention to provide dermal formulations of novel esters and amides of 9-cis-retinoic acid.

Another object of the invention is the treatment of a variety of skin conditions and diseases with formulations of novel esters and amides of 9-cis-retinoic acid.

Still another object of the present invention is to provide a method for altering the structure and appearance of the skin through the use of novel esters and amides of 9-cis-retinoic acid.

BRIEF SUMMARY OF THE INVENTION

In the present invention, 9-cis-retinoic acid and its esters and amides are synthesized and formulated for administration for the treatment of skin conditions and diseases without the inducement of dermatitis wherein there is applied topically to the epidermis of the skin a non-irritating retinoid comprised of the esters and amides of 9-cis-retinoic acid, the retinoids having the formulae:

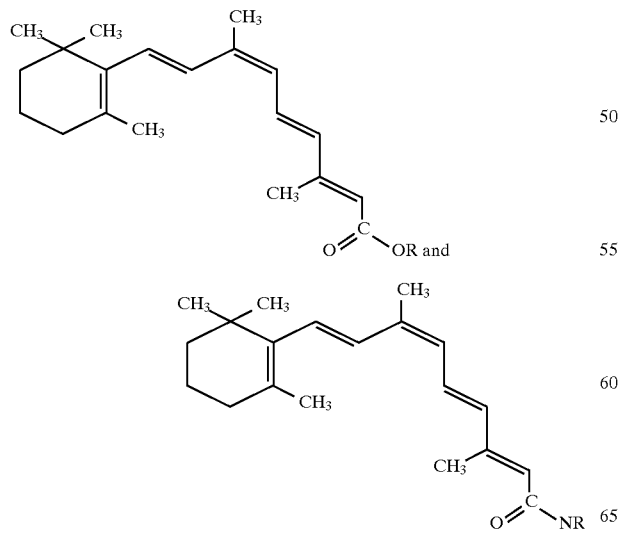

wherein X is $-H, -F, -Cl, -Br, -I, -OH, -OR, -OR', -O\overset{O}{\underset{\|}{C}}R'.$ $-\overset{O}{\underset{\|}{C}}R', -\overset{O}{\underset{\|}{C}}H, -CN, -NO_2, -NH_2, -NHR', \text{ or } NR'_2;$ wherein n is a number from 1 to 5;
wherein R' is H or any of the lower alkyls ranging from $C_1$ to $C_6$;
wherein R" is $-\overset{O}{\underset{\|}{C}}OR', -OR', -\overset{O}{\underset{\|}{C}}R', \text{ and } -R':$ or R';
wherein R'" is the hydrocarbon backbone of fatty acids;
wherein R"" is R" or the hydrocarbon backbone of fatty acids;
wherein R""' is the lower alkyls ranging from $C_1$ to $C_6$; and further,
when there are two or more R', R", R'", R"", or R""' groups attached to the same carbon, each R", R", R'", R"", or R""' group may be the same as or different from the other R', R", R'", R"", or R""' groups attached to that carbon.

DETAILED DESCRIPTION

This invention is directed to novel derivatives of 9-cis-retinoic acid which are useful in the treatment of acne and the like, but which minimize the irritating side-effects associated with 13-cis-retinoic acid and all-trans-retinoic acid and many of their esters and amides as used in treatments of acne and related dermal indications. The derivatives have the formulae:

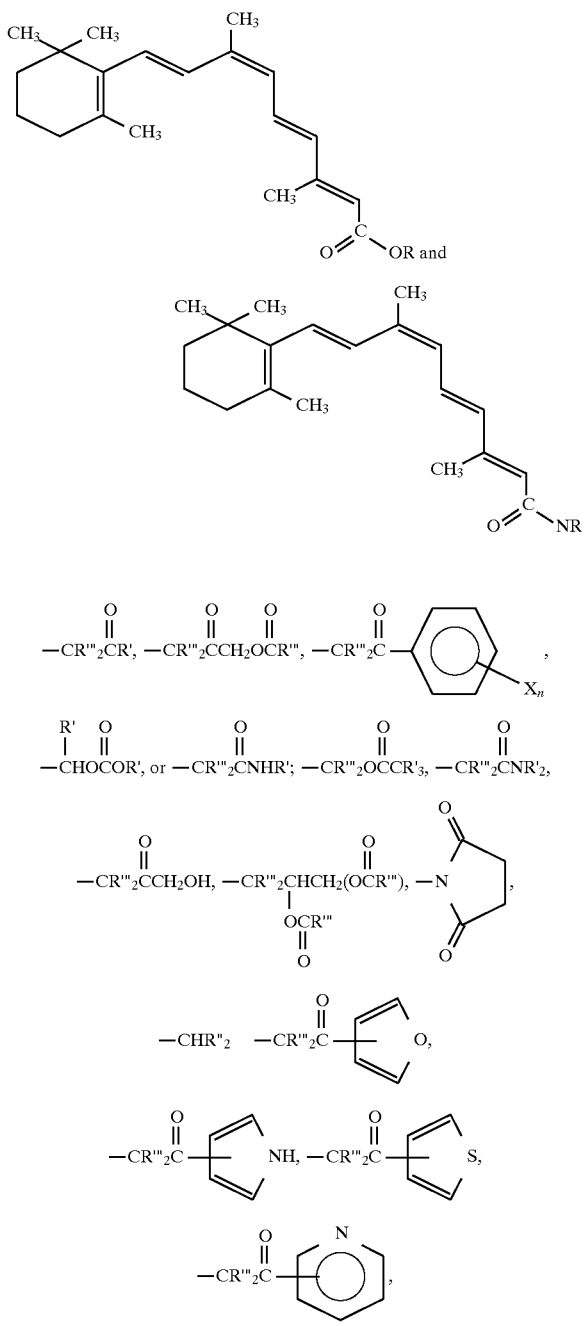

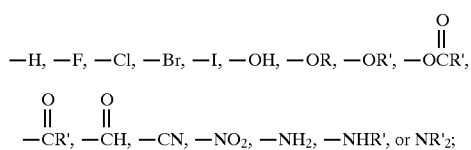

wherein n is a number from 1 to 5;

wherein R' is H or any of the lower alkyls ranging from $C_1$ to $C_6$, wherein R" is

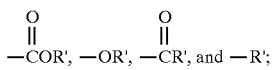

or R':

wherein R''' is the hydrocarbon backbone of fatty acids:

wherein R'''' is R" or the hydrocarbon backbone of fatty acids;

wherein R''''' is the lower alkyls ranging from $C_1$ to $C_6$; and further, when there are two or more R', R", R''', R'''', or R''''' groups attached to the same carbon, each R', R", R''', R'''', or R''''' group may be the same as or different from the other R', R", R''', R'''', or R''''' groups attached to that carbon.

The esters and amides of 9-cis-retinoic are not per se known to the art. Illustrative compounds include:

1-(9-cis-retinoyloxy)-2-propanone,
1-(9-cis-retinoyloxy)-3-decanoyloxy-2-propanone,
1,3-bis-(9-cis-retinoyloxy)-2-propanone,
1-(9-cis-retinoyloxy)-2-pinacolone,
2-(9-cis-retinoyloxy)-acetophenone,
9-cis-retinoyloxy methyl 2,2-dimethyl propanoate,
2-(9-cis-retinoyloxy)-n-methyl-acetamide,
1-(9-cis-retinoyloxy)-3-hydroxy-2-propanone,
1-(9-cis-retinoyloxy)-2,3-dioleoylpropanone, and
succinimidyl 9-cis-retinoate.

The structure of 9-cis-retinoic acid is shown in Formula 1:

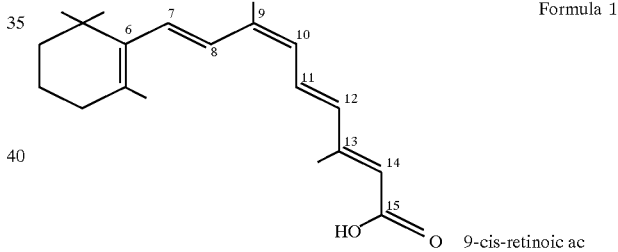

For comparison, the structure of all-trans-retinoic acid and 13-cis-retinoic acid are shown in Formulae 2 and 3, respectively:

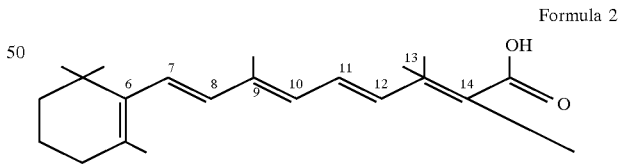

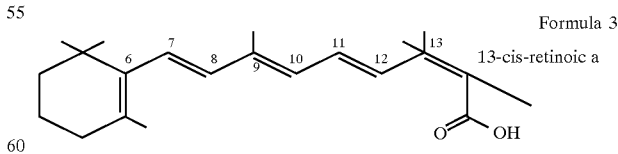

Topical Assay

A topical assay to test for pseudocomedone (utriculus) reduction in the rhino mouse is conducted.

Each test compound and a vehicle control is applied topically to the dorsal trunk of the rhino mouse. The utriculus diameters are measured with a ocular micrometer. The assay is based upon the work of Kligman, et al. (1979)

and Van Scott (1972). Kligman, et al., The Effect on Rhino Mouse Skin of Agents which Influence Keratinization and Exfoliation, J. Invest. Derm. 73: 354–358 (1979). Van Scott, Experimental Animal Integumental Models for Screening Potential Dermatologic Drugs, In Pharmacology of the Skin, eds. Montagna et al., New York, Appleton-Century-Crofts, 1972, pp. 523–533. Mann, Hair Loss and Cyst Formation in Hairless and Rhino Mutant Mice, Anat. Rec. 170: 485–500 (1971). Mezick, et al., Topical and Systemic Effects of Retinoids on Horn-Filled Utriculus Size in the Rhino Mouse. A Model to Quantify Antikeratinizing Effects of Retinoids, J. Invest. Derm. 83: 110–113 (1984). Mezick, et al., Anti-Acne Activity of Retinoids in the Rhino Mouse, In Models in Dermatology, eds. Maibach, et al., Basel, Karger, 1985.

The dorsal trunk of the rhino mouse is the test site. Each test compound is dissolved in alcohol:propylene glycol (70:30, v:v) or other suitable vehicle and topically applied (0.1 ml) to the dorsal trunk once daily, five consecutive days/week for two weeks. Also, administration may be oral (p.o.) in a suitable vehicle. Following treatment, the animals are sacrificed by cervical dislocation. The treated dorsal trunk skin is removed from the animal and placed into 0.5% acetic acid for up to 18 hours at approximately 4° C. After this, the epidermis with the acne cysts is separated from the underlying dermis. The sheets of epidermis are processed by routine methods to permanent whole mounts for microscopic examination. Also, full-thickness samples may be taken, stained (H&E), and examined by light microscopy.

The utriculus diameters are measured with an ocular micrometer to compare effects of test compounds to vehicle control and/or reference compound on cyst reduction. Light microscopy is used to determine effects on cell differentiation. The results are summarized in Table 1:

TABLE 1

TOPICAL RHINO MOUSE ASSAY

| RETINOID | % CONCENTRATION | UTRICULUS REDUCTION |
|---|---|---|
| Compound 1 | 0.1 | +++ |
| Compound 2 | 0.1 | +++ |
| all-trans-retinoic acid | 0.1 | ++ |

All-trans-retinoic acid is used as a control.
Compound 1 and Compound 2 have the formulas identified in Examples 1 and 2 below.
+ = slight activity
++ = moderate activity
+++ = substantial activity From the results it can be seen that the compounds of the invention are effective in topical applications. The data presented is raw data which does not take into account the differences in molecular weight between the compounds of the invention and all-trans-retinoic acid.

The compounds of the present invention are synthesized from 9-cis-retinoic acid. The acid is itself synthesized by the method of Boehm, et al., supra.

The preparation of the compounds of the present invention is illustrated by the examples.

Melting points are determined on a Thomas-Hooever capillary point apparatus, 1H-NMR spectra are taken with a Varian EM-360-A spectrometer, and elemental analysis is done by Atlantic Microlab, Inc., of Atlanta, Ga.

These derivatives can be applied topically or orally without causing irritation or with less irritation than found with state of the art retinoid based treatments, and are an effective and safe treatment for a wide diversity of dermal conditions, i.e., acne vulgaris, cystic acne, hyper-pigmentation, hypo-pigmentation, psoriasis, dermal and epidermal hypoplasia and keratoses, the reduction of wrinkling of the skin as an incident of aging and actinic damage, normalization of the production of sebum, the reduction of enlarged pores, promoting the rate of wound healing, limiting of scar tissue formation during healing and the like. They are additionally useful for treatment or amelioration of the same additional classes of skin disorders as is retinoic acid itself and other retinoids. These disorders include ichthyoses (e.g., ichthyosis hystrix, epidermolytic hyperkeratosis, and lamellar ichthyosis), follicular disorders (e.g., pseudofolliculites, senile comedones, nevus comidonicas, and trichostatis spinulosa), benign epithelial tumors (e.g., flat warts, trichoepithelioma, and molluscum contagiosum), perforated dematoses (e.g., elastosis perforans seripiginosa and Kyrles disease), and disorders of keratinization (e.g., Dariers disease, keratoderma, hyperkeratosis plantaris, pityriasis rubra pilaris, lichen planus acanthosis nigricans, and psoriasis). The esters and amides of 9-cis-retinoic acid are also effective for the non-irritating treatment of effects attributable to aging and particularly to photodamage and photoaging. The use of these compounds extends to non-irritating treatments involving the retardation and reversal of additional dermal and cosmetic conditions which are ameliorated by tretinoin such as the effacement of wrinkles, improvement in appearance, namely color and condition of the skin, spots caused from exposure to the sun as well as other skin disorders.

For many years the medical community has devoted a considerable amount of research time and effort to discovering new and better ways of promoting healing of wounds. Of particular concern are wounds such as burns, ulcers and corneal wounds which are difficult to treat and have a long time for complete healing. Research efforts have been devoted to discovering new ways of increasing the rate of healing wounds to minimize the risk of infection and reduce the painful period of recovery. There is a need in the medical community for pharmaceutical compositions that can be easily applied to wounds and increase their rate of healing.

It is known that retinoids can increase the rate of wound healing.

Retinoids have sometimes been defined narrowly as comprising simply vitamin A (retinol) and its derivatives such as vitamin A aldehyde (retinal), vitamin A acid (retinoic acid), comprising the so-called natural retinoids. However, recently the retinoids have been defined as a much larger class of chemical compounds that have physiochemical similarities to vitamin A and its derivatives. An example of a wound-healing retinoid is all-trans retinoic acid which is also known as tretinoin.

Tretinoin showed a rate of healing of 6% when the skin of pigs was pre-treated with a 0.05% tretinoin cream for 10 days prior to partial-thickness skin wounding. Applying tretinoin after wounding had a deleterious effect on healing. Hung et al., Arch. Dermatol. 125:65–69 (1989) believe that this deleterious effect is due to the inflammation that is caused by tretinoin.

Kligman, J. Am. Acad. Dermatol., 15779–85 (1986) studied hairless mice by irradiation with a sun lamp. The mice were then treated topically with various concentrations of tretinoin for several weeks. The subepidermal repair zone in the treated mice was significantly wider than that in the untreated control group. The collagen was histochemically and ultrastructurally normal; fibroblasts were numerous and morphologically hyper-active.

Klein, Acta. Dermatovener (Stockholm) 74:171–74 (1975) found that the skin of rats pre-treated with 1% tretinoin for 3 days before and 0.1% after the wound was made accelerated healing by 18% when compared to the control group. The skin excision included the panniculus cornices down to the fascia of the spinal musculature. Only 0.1% tretinoin was used postoperatively to prevent a worsening of dermatitis which always occurred after the preliminary treatment with tretinoin.

Ubels et al., Am. J. Ophthalmol., 95:353–58 (1983) treated experimental corneal epithelial wounds in rabbits. Treatment with 0.1% tretinoin three times per day resulted in a 21% increase in the healing rate compared to the control eyes. Treatment five times a day resulted in a 35% increase in the healing rate.

Hunt, J. Am. Acad. Dermatol. 15:817–21 (1986) reviewed vitamin A and wound healing. He states that, although few comparative studies have been done, tretinoin appears to be the most wound-active retinoid.

The effectiveness of topical tretinoin has been known for some time, but its chief drawback has been local primary irritation. It is the cutaneous safety of tretinoin rather than the systemic toxicity potential that is the cause for concern (See Papa, C., Acta Dermatovener (Stockholm) 74:128–32 (1975)). Advances in the development of newer dosage forms have increased the number of patients who can tolerate topical tretinoin, but the dermatitis caused by tretinoin is still an unwanted side reaction. Weiss et al., JAMA 259:527–32 (1988), in their study on treatment, found that 92% of the patients experienced dermatitis. To mitigate this inflammation, some patients required potent topical steroids (flucinonide or desoximatasome).

The venous ulcer is the most common leg ulcer. Lewis, Custis 44:123–24 (1989), states that venous ulcers are not a skin problem, but a problem of disordered circulation. From his clinical experience, the best treatment is the application of external pressure to counteract the high pressure transmitted through incompetent perforating veins from the deep venous system to the venules of the skin.

Rustin et al., Brit. J. Dermatol. 120:101–105 (1989), found that a vasodilator, Ketanserin, healed the lesions in a patient with recalcitrant ulceration of both lower legs diagnosed as being due to live-diploid vasculitis. As discussed above, tretinoin can accelerate skin healing, but what might be more important for some leg ulcers is Klingman's supra (1986) findings that topical tretinoin augmented the repair of ultraviolet damaged tissue in the hairless mouse with new blood vessel formation. A retinoid may have utility in treating leg ulcers by stimulating new blood vessel formation and inducing skin growth.

Retinoids affect the differentiation, maintenance and priliferation of many cell types whether they are of ectodermal, endodermal or mesodermal origin; or whether they are epithelial, fibroblastic or mesenchymal. For a review of prior developments in retinoid therapy, see Pawson, A. A., et al., J. Med. Chem., 25:1269–1277 (1982). A more recent discussion of retinoids in research and clinical medicine can be found in the publication of a symposium held in Geneva: J. H. Saurat, Editor, Retinoids, New Trends in Research and Therapy, Karger publishing Co. (1985).

Several researchers have presented experimental results which suggest that retinoic acid increases the mitogenic activity of epidermal growth factor and its binding to its cell surface receptors in vitro. For example, see Jeten, A. M., J. Cell Physiol., 110(3):235–40 (1982): Harper, R. A., et al., Endocrinology, 107(6):2113–2114 (1980); and Roberts, A. B., et al., Cancer Res., 44:1635–1641 (1984). One investigator has suggested that the effect of retinoids on the binding of EGF to its receptor is that the retinoids increase the number of EGF receptor sites and therefore enables the binding of a greater number of EGF molecules to the receptors. See, Jetten, A. M., Nature, 284:626–629 (1980); and Jetten, A. M., Fed. Proc., 43(1):134–139 (1984).

Brown et al., New Eng. J. Med., 321:76–79 (1989) demonstrated that the topical application of epidermal growth factor accelerates the rate of epidermal regeneration of partial-thickness wounds and second-degree burns. Paired donor sites were created in patients who required skin grafting either for burns or reconstructive surgery. One donor site from each patient was treated topically with silver sulfadiazine cream and one was treated topically with silver sulfadiazine containing epidermal growth factor. Total healing time in these 12 patients was 9–21 days with an average of 12 days. The healing time of the donor sites that received the epidermal growth factor was accelerated by an average 1.5 days.

Hunt and La Van, New Eng. J. Med., 321:111–112 (1989), commenting on the work of Brown et al., state that a 15% acceleration of the healing time of a patient with burns may save many days of pain or hospitalization.

Sheffield, W. et al. in EPO 339,905-AZ, discloses a wound healing composition comprised of at least one polypeptide growth factor having human metagenic or angiogenic activity at least one retinoid. The composition is reputed to have a synergistic effect with respect to growth factors and retinoids alone.

However, growth factors exist as natural molecules on very small quantities and require expensive recombinant DNA technologies to produce quantities in pharmaceutically useful amounts. Although tretinoin can be produced using sufficiently inexpensive technology to be commercially viable, it is limited by its local primary irritation.

The compositions of the present invention may be topically applied to the wound site in any suitable pharmaceutically acceptable vehicle, for example, a liquid carrier such as propylene glycol ethanol, propylene glycol ethanol chloroform, and the like. A preferred liquid composition is a solution of a small amount of at least one of the compounds in combination with from about 25 to about 75% by volume of 95% ethanol and from about 75 to about 25% by volume of liquid glycol. A typical solvent carrier of this type comprises 75% by volume 95% ethyl alcohol and 30% by volume propylene glycol. The preferred concentration of the active compound in these compositions is at least 0.01% by weight, most preferably from about 0.1% to about 0.5% by weight and most preferably from about 0.05% to about 0.2% by weight, but any therapeutically effective concentration may be used.

The compositions of the present invention may also be formulated in any number of other ways, depending on whether an aqueous solution, cream or ointment is desired and whether it would be used/and its site of use set as on the surface of the skin or in the eye.

Compositions formulated as a cream may contain a cream stabilizer such an xanthene gum, an emulsifier preferably a non-ionic emulsifier, at least one liquid and one solid hydrophobic material selected from the liquid and solid fatty acids, fatty alcohols, fatty acid esters, pharmaceutical grades of waxes and hydrocarbons, the latter ranging from liquids through semi-liquids such as petrolatum, to solids and the likes, preservative, an antioxidant, and water.

The compositions of the present invention are useful in eye drop formulations, eye gels, eye creams, lyposome or micelle formulations, acquest vehicles for soaking soaked gauze dressings, burn dressings, artificial skins, sutures and staple coatings, ointments, lotions or creams, gel formulation, foams and the like. Additional materials such as buffers, preservatives, adjusting agents, antioxidants, polymers for adjusting viscosity or for use as extenders and excipients may be used in the compositions. Methods for increasing the rate of healing a wound comprises applying or contacting the compositions of the present invention directly to the wound. The composition is permitted to remain in contact with the wound for a period of time sufficient to increase the rate of cell growth at the wound site. Such methods include incorporating any composition of the present invention into a cream formulation or soaking a gauze dressing with an acquest solution of the composition and then applying the cream or soaked gauze to a wound site such as a burn, donor site wound, ulcer or any type of cutaneous wound. Additionally, sutures or staples may be coated or soaked with the acquest composition and used to close an open wound.

The type of wounds that may be healed using the composition of the present invention are those which result from any medical or accidental injury which causes epithelial damage such asophthalmic wounds, such as those which result from corneal ulcers, cutaneous wounds, such as burn wounds, donor site wounds from skin transplants and ulcers. Additionally, dermatological conditions in which the skin has been damaged may be treated with the compositions of the present invention. Leg and foot ulcers may also be treated with compositions of the present invention. Any wound that does not result in total skin loss but retains a portion of the dermis may be treated using the compositions of the present invention.

The causes and mechanisms of psoriasis and psoriatic conditions are not fully known. The disease is genetic, and has been associated with increased levels of certain histocompatibility antigens. It has been reported that persons with elevated HLA-Cw6 are 9 to 15 times more likely to develop psoriasis than others. No cure is known, and persons with the disease experience lifelong, periodic eruptions of scaly plaques, papules and, in some persons, pustules, which may appear on any dermal surface. The disease may be exacerbated by some important drugs, including lithium, Beta-blockers, and antimalerials. Treatment with systemic steroids provide rapid clearing of psoriasis, but often cause a worsening manifestation of the condition when the medication is withdrawn, in a rebound phenomenon, which has led to the abandonment of corticosteriods as a routine treatment.

For many individuals, the clinical manifestations are associated with emotional components, which often result in attempts at concealment, self-consciousness and the avoidance of diagnosis and treatment.

By various estimates, psoriasis occurs in from 1 to 3 percent of the population worldwide. In the United States, it has been estimated that five hundred to six hundred thousand patients consult physicians each year for psoriatic conditions.

Clinically diagnosed psoriasis is treated with a variety of procedures and agents. Most commonly, topical applications of steroids, anthralin, coal tar formulations, intralesional injections of steroids, occlusive dressings employed with topical formulations, and the administration of ultraviolet light (both UVB and, less commonly, UVA are employed in combination with anthralin, coal tar formulations, and photosensitizers, such as psoralens) are employed.

There are a variety of systemic treatments employed as well, including the administration of methotrexate, hydrea, etretinate and cyclosporin.

Typically, the treatment of psoriasis involves a balancing of short term palliation and limited benefits of the more benign treatments against the greater potency and more serious side effects and consequences of the more efficacious systemic treatments.

Ultraviolet light treatments are generally effective and involve a minimum of side effects, but require a large number of office visits; unsupervised self-administration of UVB and UVA with photosensitizers is extremely unsafe and is not prescribed.

As with all antipsoriatics, the mode of action is not certainly known, but is believed be through the binding of one or more enzymes, or through the inhibition of binding of one or more enzymes (competitive binding).

A variety of enzyme mediated pathways are under investigation as the basis for psoriasis. Thus far, the evidence in the art is suggestive, but not fully probative, of several mechanisms, as discussed infra.

As in the case of other therapeutic modalities, the mode of action of the compounds of the present invention is not known. The compounds of the present invention are believed to be potent inhibitors of lipoxidase.

Each of the compounds synthesized in the present invention has been screened for topical activity. While the data obtained are set out in detail below, in general terms, all the claims evaluated as having substantial topical activity, at least comparable to the best results observed with the systemic therapies of the prior art.

There are two animal models in common use in the art at the present time. These are the customary mouse ear edema test and the less common hamster model.

The mouse ear edema model is based on the induction of edema by the topical administration of arachadonic acid to the dermis of the ear of the specimen.

A more recently developed model, which has achieved less acceptance as a predictive screen in the evaluation of potential antipsoriatic agents, is the hamster model. The procedure of the hamster model is discussed in detail, infra.

All the compounds synthesized in the present invention have been evaluated in the mouse ear edema model, and have shown substantial levels of activity. No adverse reactions have been observed.

A few of the compounds of the present invention have also been evaluated in the hamster model. The activity has been confirmatory of that observed in the mouse ear edema screen. Again, no toxic or adverse effects have been observed.

The compounds of the present invention are readily formulated with conventional pharmaceutical carriers, and may be conveniently administered by any convenient route, including im, iv, ip, subcutaneous and intralesional (local) injections, oral administration, and topical (dermal) application, with or without occlusion.

Administration in known animal models commonly recognized in the art as reasonably predictive of antipsoriatic activity have shown potent anti-inflammatory action. The most widely recognized and employed antipsoriatic screen, the mouse ear edema test, described above, shows activity which equals or exceeds that of most other therapeutic modalities which can be screened in this model.

At the same time, no adverse side reactions, toxicities or adverse indications have been observed to date.

$LD_{50}$ values by oral administration in rats illustrates that the compounds of the present invention do not represent a substantial threat of acute toxicity.

Thus in practicing the treatment of skin in accordance with the practice of the present invention, the esters and amides of 9-cis retinoic acid are topically applied to the skin site exhibiting characteristics to be treated in any suitable pharmaceutically-acceptable vehicle, as for example, a liquid carrier such as propylene glycol-ethanol. A preferred liquid composition is a solution of a small amount of at least one of the compounds of the invention in a combination of (A) from about 25% to about 75% by volume of 95% ethanol and (B) from about 75% to 25% by volume of a liquid glycol.

A typical solvent carrier of this type comprises 70% by volume 95% ethyl alcohol and 30% by volume propylene glycol. A small but effective amount of an antioxidant such as butylated hydroxytoluene may also be included in the composition. A typical solvent carrier of this type comprises 70% by volume 95% ethyl alcohol and 30% by volume propylene glycol. An antioxidant at a concentration of 0.01 to about 0.1% by weight may be incorporated in the carrier.

The preferred concentration of the active compound in these compositions is at least about 0.01% by weight, more preferably from about 0.01% to about 0.5% by weight and most preferably from about 0.05% to about 0.2% by weight, but any therapeutically effective concentration may be used. Concentrations less than 2.5% by weight will normally be employed.

Such topical formulations will generally be made up to contain from about 0.025 to about 2.5 weight percent of the active 9-cis-retinoid, preferably from about 0.05 to 0.5 weight percent, although in most circumstances the concentration is not narrowly critical. The compounds are both highly potent and highly safe, and an exceptionally wide range of concentrations may be employed as indicated.

It is also possible, although generally less preferred to administer the retinoids of the present invention orally, or even parenterally, subcutaneously or, if desired, intravenously. Such systemic administration produces systemic effects which are not generally preferred, as higher dosages may be required to achieve the required therapeutic levels to produce the desired action. When administered systemically, the concentrations to be employed may range widely, from 0.5 to 50 milligrams per kilogram of body weight.

The compounds are sensitive to ultraviolet light, and are oxidized when exposed to air and heat or other oxidizing conditions.

Like most retinoids, the compounds of the present invention are highly hydrophobic in character, and formulation of the compounds requires that these characteristics be taken into account.

A further advantage of the compounds is their non-irritating characteristic when applied topically. This highly desirable characteristic is not seen when all-trans-retinoic acid is used.

The 9-cis-retinoic acid on which the present invention is based is per se known. Boehm, et al., J. Med. Chem., Vol. 37, No. 3, pp. 408–414 (1994).

Boehm et al. demonstrate that 9-cis-retinoic acid is more efficient at binding the two known sub-families of intracellular receptors and each of the three defined sub-types within each of the subfamilies, and predict that 9-cis-retinoic acid will provide improved therapeutic indices when compared to other retinoic acids (i.e., all-trans-retinoic acid and 13-cis-retinoic acid).

Competitive binding studies show 9-cis-retinoic acid has the lowest equilibrium constants of all retinoids for all six subfamilies of retinoid receptors.

Boehm et al. hypothesize that 9-cis-retinoic acid is an endogenous isomer of the retinoid family of biologically active retinoids occurring in vivo.

The activation of the retinoid receptors has been associated with induced or accelerated mitosis of normal skin cells, and it is the induced cell growth, particularly epithelial cell growth, which is most often associated with the improved skin properties occurring with use of retinoids to treat the skin.

Abnormal skin cells, i.e., those characterizing photodamaged or age damaged skin, neoplasia and keratoses, cells in hyperpigmented skin regions, psoriatic skin cells, and the like, have been associated with defective or compromised retinoid receptors. It is thus hypothesized that treatment of the skin with retinoids functions to stimulate mitosis and proliferation of normal cells, while the abnormal cells are not stimulated and do not participate in the increased levels of mitosis. As the process of stimulated mitosis continues over time, accompanied by the normal death and sloughing off of cells at the surface of the skin, the abnormal cells associated with the foregoing conditions are preferentially replaced by normal cells.

The enhanced binding of all the types of receptors of the 9-cis-retinoic acid is thus a direct basis for predicting a high therapeutic index compared to other retinoid acids.

Along with the heightened binding activity of the 9-cis-retinoic acid comes an equally inflammatory and irritating qualities of retinoids. Thus, by the data shown by Boehm et al., increased potency is expected to be accompanied by comparably or equally heightened side effects which limit the safety of the retinoids. The prediction of a higher therapeutic index is also a prediction of higher safety problems.

We have found that esters and amides of the 9-cis-retinoic acid do not show any detectable irritation or inflammation of the skin among users. The activity of the esters and amides is, however, comparable in magnitude with the 9-cis-retinoic acid itself and substantially increased in comparison with all-trans-retinoic acid and 13-cis-retinoic acid. We achieve increased effectiveness, similar to that projected by Boehm, et al. for the 9-cis-retinoic acid, but without the correlative increase in hazards. As a consequence, a greatly improved therapeutic profile is achieved without safety problems.

EXAMPLES

Example 1

Synthesis of compound 1:

1-(9-cis-retinoyloxy)-2-pinacolone

Into a 100 ml round bottom flask is added 1.0 g (0.0033 moles) 9-cis-retinoic acid, 25 ml of anhydrous methanol, and 0.2 g (0.0035 moles) of KOH. The solution is stirred at room temperature until the 9-cis-retinoic acid dissolves. After the solvent is removed under vacuum, 25 ml of acetonitrile is added and the solution is again concentrated to a semisolid under vacuum. Chloroacetone, (2.0 g, 0.032 moles), 0.1 g 18-crown-6 (0.00038 mole), and 100 ml of acetonitrile are added. The solution is stirred for 24 hours at room temperature with a magnetic stirrer. The sample is concentrated to about 5 ml and chrnmatographed on a neutral aluminum oxide (Aldrich #19,997-4) column (14× 1.8 cm). The alumina is deactivated with 20 ml of water per 1.0 kg of alumina.

The sample is eluted stepwise with 100 ml of 20% dichloromethane in hexane, 100 ml of 50% dichloromethane in hexane, and finally with 250 ml of dichloromethane. The sample elutes quickly and the vast majority of the impurities remain on the column. Fractions of 25 ml are collected and evaluated by thin layer chromatography (TLC) on silica gel (EM Reagents #5775) develop with ethyl acetate:heptane (1:3). The fractions containing the product are combined and concentrated to give an orange oil which solidifies on cooling to give 0.55 g of solid.

Triturating the sample with 10 ml of cold 95% ethanol produces a sharp melting point.

TLC on silica gel (EM Reagents #5735) develop with 1:3 ethyl acetate:heptane shows one spot, $R_f$=0.41. TLC on aluminum oxide (EM Reagents #5581) develop with 1:3 ethyl acetate:heptane shows one spot, $R_f$=0.73.

The NMR (CDCl3) spectrum of Compound 1 is identical to the spectrum of 9-cis-retinoic acid except for two additional peaks and the lack of a carboxylic acid peak. The two additional peaks are (singlet, 2 protons, —OCH2 CO—) and (singlet, 3 protons COCH3). The structure is confirmed by NMR.

Elemental analysis for the compound gives a theoretical value for $C_{23} H_{32} O_3$ of 77.49% C, 9.05% H; the found values are 77.52% C and 9.17% H.

Example 2
Synthesis of Comoound 2:
  2-(9-cis-retinoyloxy)-4'-methoxyacetophenone
The procedure used in Example 1 is followed with minor modifications.

The reaction is carried out in a 250 ml round bottomed flask with 1.0 g of 9-cis-retinoic acid and a 20% molar excess of 2-chloro-4-methoxyacetophenone. (2-chloro-4-methoxyacetophenone is prepared from the Friedel-Crafts acylation of anisole with chloroacetic anhydride.) After completion of the reaction, the product is isolated by column chromatography under the same conditions as in Example 1 except that a larger column (11 cm×4 cm diameter) is used. The product at this point, however, contains unreacted 2-chloro- 4-methoxyacetophenone. A homogeneous product is obtained by recrystallization form 100 ml of 95% ethanol to give 0.88 g of a yellow solid.

TLC on silica gel (EM Reagents #5735) develop with 1:3 ethyl acetate:heptane shows one spot, $R_f$=0.45. TLC on aluminum oxide (EM Reagents #5581) develop with 1:3 ethyl acetate:heptane shows one spot, $R_f$=0.69.

The NMR (CDCl3) spectrum of Compound 2 is identical to the spectrum of 9-cis-retinoic acid except for three additional peaks and the lack of a carboxylic acid peak. The structure is confirmed by NMR.

Elemental analysis for the compound gives a theoretical value for $C_{29} H_{36} O_4$ of 77.64% C, 8.09% H; the found values are 77.58% C and 8.10% H.

Example 3
Synthesis of Compound 3
  1-(9-cis-retinoyloxy)-3-decanoylyoxy-2-propanone
The following synthetic scheme is used for the synthesis of Compound 3.

Into a 500 ml round bottom flask fitted with a reflux condenser and magnetic stirrer is added 20 g (0.22 mole) of dihydroxyacetone dimer, 300 ml of acetone, 30 ml of DMF, and 30 ml of pyridine and 14 g (0.078 mole) of decanoyl chloride. The dihydroxyacetone dimer dissolved as the acid chloride is added. The solution is refluxed for 30 min. and then stirred for 1 hr. The reaction is poured into 2 l of cracked ice and allowed to stand for 2 hrs. as the product crystallized. The solid is collected, dissolved in dichloromethane and dried ($Na_2SO_4$). The solid contained large quantities of water which had to be removed. The dichloromethane is removed under vacuum and the oil is dissolved in acetone and placed in the freezer (−10° C.) overnight. The disubstituted dihydroxyacetone impurity separated and is removed. Sufficient water is added to make the solution about 25% water by volume and after standing overnight in the freezer, the product separated and is recrystallized from dichloromethane/hexane to give 5.2 g.

TLC on silica gel developed with 4/1 heptane/ethyl acetate, visualized with iodine, showed the product to be homogeneous. NMR (CDC13/DMSO-D6) showed the correct ratio for $OCH_2COCH_2$—protons to $C_9H_9$ protons. The NMR spectrum is complex as is the NMR spectrum of dihydroacetone.

Into a 100 ml round bottom flask equipped with a reflux condenser and a magnetic stirrer is added 2.5 g (0.01 mole) of the above alcohol and 15 ml of thionyl chloride. The solution is refluxed for 70 min and the unreacted thionyl chloride is removed under vacuum. Toluene, 25 ml, is added and removed under vacuum to remove the last traces of thionyl chloride. The remaining oil solidified on cooling and is recrystallized from 15 ml of hexane to give 1.45 g (54% yield). The structure is confirmed by NMR.

The coupling of the alkyl chloride to 9-cis-retinoic acid is carried out as described for Compound 1. Using equal molar concentration of the above chloro compound and 9-cis-retinoic acid a yield of 41% can be obtained. TLC indicates the sample to be homogenous. Using the same conditions as described for Compound 1, on silica gel $R_f$=0.69 and on aluminum oxide $R_f$=0.37. The NMR spectrum of the product is essentially the combined spectra of the two reagents, 9-cis-retinoic acid and the substituted chloromethyl ketone, which are coupled to give Compound 2. There is one minor change, however. The peak for (COCH Cl) disappears and the methylene hydrogens (of $COCH_2Cl$) had shifted where 2 singlets appeared and are separated by about 0.02 ppm (4 protons, —$CO_2CH_2COCH_2OCO$—). The structure is confirmed by NMR.

Example 4
Synthesis of Compound 4
  1,3-bis-(9-cis-retinoyloxy)-2-propanone
The procedure for Compound 1 is used for Compound 4 with minor changes. Instead of chloroacetone, 1,3-dichloroacetone (0.2 g, 0.0016 mole) is used. The solution is stirred for 24 hrs. before chromatography. The reaction is worked up as described for Compound 1 to give 1.41 g (38% yield). After triturating with 2×2 ml hexane the melting point increased and sharpened. TLC indicated sample to be homogenous. Using the same conditions as described for Compound 1, on silica gel $R_f$=0.67 and on aluminum oxide $R_f$=0.42. NMR (CDC13) spectrum of Compound 3 is identical to the spectrum of 9-cis-retinoic acid except for the additional peak (singlet, 2 protons, —$OCH_2CO$—). The structure is confirmed by NMR.

Example 5
Synthesis of Compound 5
  9-cis-retinoyloxy methyl phenyl ketone
The procedure for Compound 1 is used for Compound 5 with minor changes. Instead of chloroacetone, alpha-chloroacetophenone is used. The structure is confirmed by NMR.

Compound 5 is similar to Compound 1, except that the terminal methyl group has been replaced with a phenyl group. This will allow molecular modification by phenyl group substitution in order to spread the physicochemical properties of the derivatives for Quantitative Structure-Activity Relationship (QSAR) studies (Purcell et al., Strategy of Drug Design: A Molecular Guide to Biological Activity, Wiley, N.Y., 1973).

Example 6
Synthesis of Compound 6
  9-cis-retinoyloxymethyl 2,2-dimethylpropanoate
The procedure for Compound 1 is used for Compound 6 with minor changes. Instead of chloroacetone, chloromethyl pivilate is used. The structure is confirmed by NMR. Compound 6 uses the same ester derivative as the antibiotic prodrug pivampicillin in which the acyloxymethyl ester is hydrolyzed by non-specific esterases to generate ampicillin (Sinkula, Application of the Pro-Drug Approach to Antibiotics, in Pro-drugs as Novel Drug Delivery Systems, ACS Symposium Series (1974), p. 116–153).

Example 7

Synthesis of Compound 7

2-(9-cis-retinoyloxy)-N-methyl-acetamide

The procedure for Compound 1 is used for Compound 7 with minor changes. Instead of chloroacetone, N-methyl chloroacetamide is used. The structure is confirmed by NMR.

Compound 7 is designed to explore hydrophilicity: the N-methyl acetamide group is very hydrophilic (Wolfenden, Waterlogged Molecules, Science, 222: 1087–1093 (1983)).

Example 8

Synthesis of Compound 8

1-(9-cis-retinoyloxy)-3-hydroxy-2-propanone

Compound 8 is prepared by reacting the acid chloride of 9-cis-retinoic acid with an excess of dihydroxyacetone. State of the art synthetic schemes are available (Haslam, Recent Developments in Methods for the Esterification and Protection of the Carboxyl Group, Tetrahedron, 36: 2409–2433 (1980)) and can also be used as an alternative. The structure is confirmed by NMR.

Compound 8 is similar to Compound 1 with a terminal methyl hydroxyl group instead of a methyl group. This modification should make Compound 8 more glyceride-like and more hydrophilic.

Example 9

Synthesis of Compound 9

1-(9-cis-retinoyloxy)-2,3-dioleoylpropane

Compound 9 is prepared by reacting oleoyl chloride with glyceraldehyde followed by reduction of the aldehyde group with sodium borohydride. This gives a 1,2-disubstituted glyceride with an available hydroxyl for coupling. The coupling of 9-cis-retinoic acid is carried out as for Compound 8. This scheme is based on the synthetic procedure for glyceride derivatives of aspirin (Paris, et al., Glycerides as Prodrugs. 2. 1,3-Dialkanoyl-2-(2-methyl-4-oxo-1,3-benzodioxan-2-yl) glycerides (Cyclic Aspirin Triglycerides) as Antiinflammatory Agents, J. Med. Chem., 23: 79–82 (1980)). The structure is confirmed by NMR.

Compound 9 is based on evidence that topical application of glycerides is an effective means of incorporating essential fatty acids into the skin (Prottery, et al., The Repair of Impaired Epidermal Barrier Function in Rats by the Cutaneous Application of Linoleic Acid, British J. of Derm., 94: 13–21, (1976)).

Example 10

Synthesis of Compound 10

Succinimidyl 9-cis-retinoate

Compound 10 is synthesized by coupling 9-cis-retinoic acid with N-hydroxysuccinimide (Zimmerman, et al., The Effect of Active Ester Components on Racemization in the Synthesis of Reptiles by the Dicyclohexyl-carbodiimide Method, J. Am. Chem. Soc., 89: 7151–7152 (1967)). The structure is confirmed by NMR.

Compound 10 is the most easily hydrolyzed prodrug. The N-hydroxy-succinimide group gives an activated ester linkage and is used in peptide synthesis because of this property.

Example 11

Topical Assay for the Inhibition of Skin Cancers

The usefulness of the retinoid compounds of the present invention for the inhibition of skin cancers is demonstrated by testing in the ornithine decarboxylase (ODC) assay an ester Compound 1, 1-(9-cis-retinoyloxy)-2-pinacolone and Compound 2, 2-(9-cis-retinoyloxy)-4-methoxyacetophenone).

The ODC/Retinoid Bioassay is based on the method of Verma, A. K. and Boutwell, R. K., Cancer Res. (1977) 37:2196–2201. The ODC assay measures a compounds effect on the prevention of the induction of ODC, namely the effect of the retinoid compound on the inhibition of the tumor promoter 12-O-tetradecanoylphorbol-13-acetate (TPA) induced ODC activity. The assay is carried out using CD-1 mice (aged 7 to 9 weeks). The dorsal hair of the mice is shaved 3–4 days before testing. Four mice are used for each point. The test retinoids, at one of two dose levels (1.7 and 17 nmoles) dissolved in 0.2 ml of acetone is applied topically to the back of each shaved mouse. A single dose of TPA (17 nM) is applied to the back of each treated mouse 30 minutes later. Control groups are treated with either acetone alone, TPA, or tretinoin. The mice are sacrificed by cervical dislocation 5 hours after TPA treatment.

The dorsal skin encompassing the shaved and TPA exposed area is excised and placed in a 100 ml beaker containing distilled water maintained at 51° C.–57° C. The skin is soaked for 50–70 seconds at this temperature with intermittent stirring. The skin is placed epidermis side up in a chilled (0°–5° C.) stainless steel plate and the epidermal layer is scraped off with a razor blade. The epidermal layers from the 4 mice are pooled and placed in a homogenization tube with 2 ml of ODA buffer (10 nM tris-HCl with 0.050 nM pyridoxal phosphate, 0.050 nM ethylenediaminetetraacetic acid (EDTA), 1 mM dithiothreitol, pH 7.5). The pooled epidermal layers are homogenized for 15 seconds at 0° C. using a Polytron homogenizer at a setting of 7.5. The homogenate is centrifuged at 30,000×g and the supernatant fraction is pipetted into a storage tube and frozen for about 72 hours.

The homogenate is assayed for ODC activity as described by Verma and Boutwell to measure the release of $^{14}CO_2$ from labeled DL(1-14C) ornithine. Incubations are carried out in disposable centrifuge tubes with center well holders containing filter paper impregnated with sodium hydroxide to absorb $^{14}CO_2$. The incubation mixture consisted of 90 μl of L-ornithine, 350 μl of ODC buffer, 100 μl of 14C-ornithine (1.32 nm, Sp. Act:4.4 pCi/pM) and 10 μl of test sample. After incubation at 37° C. for 45 minutes, 0.5 ml of 2M chilled citric acid (4° C.) is added and incubation is continue for an additional 30 minutes to insure complete absorption of $^{14}CO_2$. The filter paper is removed from the center well holders and set in 1 ml of water in capped scintillation vials for at least 1 hour before adding RBI 3820 scintillation cocktail. Radioactivity is measured in a Tri Carb Scintillation Counter. Results are expressed as pmol of $^{14}CO_2$ released in 30 minutes per milligram of protein based on the specific activity of DL-14C-ornithine. The results are expressed in Table 2 below as the % reduction in ODC activity as compared to the control, for the compounds of each of the preceding Examples:

TABLE 2

| Compound | Concentration (nM) | ODC Activity (nM $^{14}$ CO$_2$/30 in/mg Protein) Reduction |
|---|---|---|
| 1 | 17.0 | +++ |
| 1 | 1.7 | +++ |
| 2 | 17.0 | +++ |
| 2 | 1.7 | ++ |
| 3 | 1.7 | +++ |
| 4 | 1.7 | +++ |
| 5 | 1.7 | ++ |
| 6 | 1.7 | +++ |
| 8 | 1.7 | +++ |
| 9 | 1.7 | ++ |
| 10 | 1.7 | +++ |
| Acetone | 0.0 | NA* |
| TPA | 17.0 | 0 |
| Tretinoin | 17.0 | +++ |

*NA = not applicable
+ = slight activity
++ = moderate activity
+++ = substantial activity The results recorded in the Table indicate that the retinoid compounds of the present invention possess biological activity that inhibits TPA induced ODC activity rendering these compounds useful for treating malignant skin disorders.

Example 12
Topical Assay for the Inhibition of Skin Cancers

Another topical assay is conducted following the procedure described above. All-trans-retinoic acid is used as a control. Compounds 1, 2, 5, 6, and 10 are tested The results are summarized in Table 3:

TABLE 3

TOPICAL RHINO MOUSE ASSAY

| RETINOID | CONCENTRATION | UTRICULUS REDUCTION |
|---|---|---|
| Compound 1 | 0.1 | +++ |
| Compound 2 | 0.1 | +++ |
| Compound 5 | 0.1 | ++ |
| Compound 6 | 0.1 | +++ |
| Compound 10 | 0.1 | ++ |
| all-trans-retinoic acid | 0.1 | ++ |

+ = slight activity
++ = moderate activity
+++ = substantial activity

Example 13
ORAL ASSAY

An oral assay for hamster sebaceous gland reduction is conducted.

Hamsters are dosed orally with the test compound and vehicle alone. The reduction in sebaceous gland size is estimated microscopically in relation to the control. The assay is unique and proprietary to Ortho Pharmaceutical Corp. and is based upon the work of Plewig et al. (1977) and Gomex et al. (1980). Plewig, et al., Hamster Ear Model for Sebaceous Glands, J. Invest. Derm. 68: 171–176 (1977). Gomez, et al., Effect of 13-cis-Retinoic Acid on the Hamster Flank Organ, J. Invest. Derm. 74: 392–397 (1980).

For oral (p.o.) studies, male Syrian golden hamsters are closed at 5 ml/kg, once daily, five consecutive days/week for two or three weeks. Modified but similar dosing schedules could be used. Control hamsters are dosed with vehicle alone at 5 ml/kg. Following final treatment (up to 72 hours), the hamsters are sacrificed in a CO$_2$ atmosphere. Samples of each test site are placed into 10% buffered formalin and histologically prepared. Serial sections of each sample are stained (H&E) and examined microscopically.

The reduction in sebaceous gland size is estimated microscopically in relation to the control treated sites. To quantify sebaceous gland size, cross-sectional areas are measured with an image analyzer system. The results are summarized in Table 4:

TABLE 4

ORAL HAMSTER SEBACEOUS GLAND ASSAY

| RETINOID | DOSE (mg/kg) | SEBACEOUS GLAND REDUCTION |
|---|---|---|
| Compound 1 | 32 | +++ |
| Compound 2 | 32 | +++ |
| Compound 3 | 32 | +++ |
| 13-cis-retinoic acid | 32 | ++ |
| all-trans-retinoic acid | 32 | +++ |

+ = slight activity
++ = moderate activity
+++ = substantial activity

From the results it can be seen that the compounds of the invention are as effective as 13-cis-retinoic acid in both topical and oral applications. The data presented is raw data which does not take into account the differences in molecular weight between the compounds of the invention and 13-cis- or all-trans-retinoic acid. If one does take this into account, as must be done to accurately compare the activity of the various compounds, it can be seen that many of the compounds of this invention are equally or more effective than either 13-cis- or all-trans-retinoic acid. A further advantage of the compounds of the invention over 13-cis-retinoic acid, is their non-irritating characteristics when applied topically. This highly desirable characteristic is not seen when 13-cis-retinoic acid is used.

Example 14
Topical Assay for Primary Acute Dermal Irritation

Compound 2 of Example 2, 2-(9-cis-retinoyloxy)-4-methoxy-acetophenone is evaluated for its potential to produce primary dermal irritation after a single topical application to the skin tissue of rabbits.

Twelve healthy, young, adult, female New Zealand White rabbits (Orycetolagus cuniculus), are used in the study. The animals are purchased from a registered commercial breeding laboratory. At the start of the study, the animals are in the weight range between 2.0 and 3.0 kilograms, and are approximately 11 weeks of age. Animals selected for the test are not subjected to any previous experimental procedures, and their skin is free from irritation, trauma and disease.

A dose of 0.5 ml of a test solution composed of 0.025 g of 2-(9-cis-retinoyloxy)-4-methoxyacetophenone in a liquid solution composed of 75 ml of ethyl alcohol, 25 ml of propylene glycol 400, and 0.025 g by weight of butylated hydroxytoluene is applied to one intact and one abraded skin site per animal. Six animals are treated in this manner.

A control group of six animals is treated in an identical manner except that 2-(9-cis-retinoyloxy)-4-methoxyacetophenone is absent from the control solution.

The application sites are prepared by clipping the skin of the trunk free of hair approximately 24 hours before application of the dose. One application site on each animal is abraded by making minor incisions through the stratum corneum, but not sufficient to disturb the derma (that is, not sufficiently deep to produce bleeding). The second application site is intact skin.

The dose is applied to a small area (approximately 6 cm²) of skin and covered with a gauze patch which is held in place with Vetrap bandaging. The patches are applied to one intact site and one abraded site per animal. The test substance is kept in contact with the skin for 24 hours. The skin is not rinsed following the 24 hour exposure period.

Animals are observed for signs of erythema and edema 24 and 72 hours after application of the test material. Observations are scored according to the Draize Scale for Scoring Skin Reactions as in Draize, J. H., Dermal Toxicity, Appraisal of the Safety of Chemicals in Foods, Drugs and Cosmetics Dermal Toxicity, pp. 46–59, Association of Food and Drug Officials of the U.S., Topeka, Kans., 1965. Observations at the different scheduled times indicates that no signs of erythema or edema formation are evident in any of the 12 test animals at any observation time period. Animals are weighed at the beginning and at the end of the observation period. All 12 animals exhibited a gain in body weight. No overt signs of toxicity are evident during the course of the study.

Example 15
Topical Assay for Comparative Dermal Irritation 2-(9-cis-retinoyloxy)-4-methoxyacetophenone is evaluated in a study of its potential to produce dermal irritation. Comparisons are made of tretinoin, isotretinoin, 2-(9-cis-retinoyloxy)-4-methoxyacetophenone, and the vehicle solution.

In the first test, four solutions are used. The control consists of vehicle solution, namely a solution of 60% by volume ethanol and 40% by volume polyethylene glycol. The other three solutions are 0.025% solutions of tretinoin, isotretinoin, or 2-(9-cis-retinoyloxy)-4-methoxyacetophenone in 60% by volume ethanol and 40% by volume polyethylene glycol. Four patients paint two saturated cotton swabs of each of the four solutions on four different areas of the inner forearm, twice daily for ten days. No irritant reactions occur.

In the second test, four other solutions are used. The control consists of vehicle solution, namely a solution of 90% by volume ethanol and 10% by volume polyethylene glycol. The other three solutions are 0.075% solutions of tretinoin, isotretinoin, or 2-(9-cis-retinoyloxy)-4-methoxyacetophenone in 90% by volume ethanol and 10% by volume polyethylene glycol. Four patients paint two saturated cotton swabs of each of the four solutions on four different areas of the inner forearm, twice daily for ten days. Only one subject experiences an irritant reaction. On day two, the tretinoin area begins reacting with redness and peeling. On day seven, the isotretinoin area begins reacting with redness and peeling. By day nine, both areas are still reacting, the tretinoin area more intensely than the isotretinoin area. There is no reaction in either the 2-(9-cis-retinoyloxy)-4-methoxyacetophenone or the control areas.

In the third test, three solutions are used. The three solutions are 0.075% solutions of tretinoin, isotretinoin, or 2-(9-cis-retinoyloxy)-4-methoxyacetophenone in 90% by volume ethanol and 10% by volume polyethylene glycol. Four patients paint two saturated cotton swabs of the 2-(9-cis-retinoyloxy)-4-methoxyacetophenone solution twice daily on one cheek of their faces. To the other cheek they apply two saturated cotton swabs of either tretinoin or isotretinoin.

The tests are carried out in double-blind fashion, that is, neither the subjects nor the investigator know the contents of the solutions during the study.

Clinical assessments are made daily of the subjects cheeks. All subjects develop irritant reactions by the third or fourth day of the study. Cheeks of subjects painted with solutions containing 2-(9-cis-retinoyloxy)-4'-methoxyacetophenone are found to be slightly irritated or not irritated at all during the six days the study is conducted. By way of contrast, the cheeks of subjects painted with solutions containing tretinoin or isotretinoin develop reactions which are so intense with redness and peeling that all subjects discontinue application on or before the sixth day of the study.

Example 16
Topical Assay for Antiaging and Antiactinic Effects

Four subjects aged 49 to 73, three females and one male having significant, easily observe, sun-damaged, wrinkled, aged skin of the face and forearms are subjects of a study to determine the effect of topical application of 2-(9-cis-retinoyloxy)-4-methoxyacetophenone in the treatment of dermatoheliosis. The three females had moderately severe sun-damaged skin and wrinkles of the forearms, hands and face. The one male (aged 73) has extremely severe sun damage in these areas as well as multiple actinic keratoses. The four subjects are provided with and applied to their entire faces (omitting the eyelids) and dorsal surface of the right forearm, once daily for 12 to 16 weeks, 0.1% concentration of 2-(9-cis-retinoyloxy)-4-methoxyacetophenone in a hydrophilic cream vehicle. The left forearm of each patient is treated daily with a non-medicated moisturizer of the patients choice.

All subjects are evaluated every 4 weeks through the study for redness, peeling, skin surface texture and wrinkling. Biopsies (using a 4 mm punch) are taken from the dorsal surface of the right upper forearm at the beginning of the study and again from the same area at the end of the study. The biopsies are stained with H & E, Alcian Blue and collagen/elastic stains and compared by a qualified dematopathologist.

Facial assessment of the patients indicates that all show an improvement in their dermatoheliosis. Two of the four patients show very significant improvement in facial smoothness, dryness and fine wrinkling. Moderate improvement of these parameters are observed in the other two patients. The improvements begin at about two months into the study and continue throughout the remainder of the study.

All the patients involved in the study are pleased by the improved appearance of their skin and note that they feel their facial skin is fresher, clearer and more attractive during the study.

Assessment of the forearms of the patients indicates that three show improvement in surface texture (smoothness), surface dryness and fine wrinkling within two months after application of the cream containing 2-(9-cis-retinoyloxy)-4-methoxy-acetophenone is initiated. This improvement is maintained throughout the remainder of the study and is readily apparent when right and left forearms are compared. The one patient who does not show improvement is found to be non-compliant with the instructions for use and uses only sparing application of the cream containing 2-(9-cis-retinoyloxy)-4-methoxyacetophenone and limits treatment to one small spot on the forearm.

No significant irritation is experienced by any patient. Very slight pinkness and a feeling of slight tightness in facial skin develops in two patients after more liberal use of the cream is encouraged.

Comparison of the biopsies taken at the onset of the study with those taken after the treatment period indicates no significant differences in before treatment and after treatment biopsies.

While this test does not have a control, the results are compared with the results obtained from a similar study conducted by Weiss et al. in which 0.1% concentration of retinoic acid in a hydrophilic cream vehicle or vehicle alone is applied to facial skin and dorsal forearm skin. In the Weiss study, it is observed that vehicle alone had no clinical or histological effect but that retinoic acid cream, after 16 weeks of use had some positive effects on the surface texture and wrinkling of sun damaged facial skin, and on the histology of the epidermal and stratum corneum layers of dorsal forearm skin. Also noted in this study is the occurrence of a moderately severe irritancy level from using retinoic acid cream.

Example 17

Tissue Culture Assays

It has been shown while investigating the effect of tretinoin on keratinocytes that tretinoin has the capacity to stimulate proliferation of quiescent keratinocytes in vitro (Varanit, et al., 1989). Varanit, et al., conclude that tretinoin stimulates keratinocyte growth, in part, by increasing epidermal growth factor receptor RNA and transforming growth factor-alpha production (Mitra et al., 1989).

The esters and amides of 9-cis-retinoic acid are evaluated using several assays developed by Nickoloff. One of the major thrusts is the delineation of the effect of various keratinocyte growth modulating factors on cultured human keratinocytes. The tissue culture assays used are given in full detail in Nickoloff, B. J., Mitra, R. S., Riser, B. L., Dixit, V. M., and Varani, J., Am. J. Pathol., 132:543–551 (1988); Nickoloff, B. J., Mitra, R. S., Elder, J. T., Fisher, G. J., and Voorhees, J. J., Brit. J. Dermatol., 121, 161174 (1989); Nickoloff, B. J. and Mitra, R. S., J. Invest. Dermatol., 1989. In the tissue culture work, the primary cultures of keratinocytes are obtained from normal appearing skin from volunteers, normal adult face-lift skin or neonatal foreskin.

Cell Proliferation Tissue Culture

When the primary cultures of keratinocytes are subcofluent (10–14 days), they are passed into plastic Petri dishes using 0.03% trypsin, 0.01% EDTA. The KGM (Keratinocyte growth medium) is replaced every 2–3 days and these cells are considered to be passage No. 1. When the keratinocytes were subcofluent, they are removed and seeded. The day of adding IFN-gamma (gamma interferon) is designated as day 0. On day 4, the medium is removed and the cells are washed once with fresh KGM and the keratinocytes are detached using 0.03% trypsin, 0.01% EDTA and an aliquot is placed into a hemocytometer for manual counting using a phase contrast microscope.

Motility Assay Agarose Drop Explant Technique

Keratinocytes removed from cultures dishes by using 0.03% trypsin, 0.01% EDTA; $10^6$ keratinocytes are centrifuged into a 0.1 ml cell pellet and resuspended in 0.3 ml of KGM containing 0.2% agarose. One to two-microliter droplets of the cell suspension are delivered with a micropipette into the wells of a microtiter culture dish. After cooling, the agarose droplets are covered with 0.2 ml of the overlay medium After incubation, migration of the cells is examined daily for 1 to 3 days by phase contrast microscopy using an Olympus phase contrast microscope. The distance to the leading edge of migrating cells from the edge of the agarose droplet is determined on four sides of each droplet.

Motility Assay—Micropore Filter Assay

Nitrocellulose filters 12m (pore diameter) are used to separate a modified Boyden chamber into two fluid-filled (KGM) compartments. Keratinocytes are placed in the upper compartment and allowed to migrate into the filters. After 20 hours, the filters are stained with hematoxylin and eosin and the number of migrating cells is determined microscopically.

Enzyme-Linked Immunosorbent Assay (ELISA)

ELISAs are used to quantify the amount of immunoreactive FN (fibronectin) TSP (thrombospondin) and LN (laminin) produced by keratinocytes and secreted into the culture medium. Briefly, cells grown in cultures dishes are washed and then incubated in KGM or KBM (growth factor-deprived keratinocyte basal medium). The culture fluids are harvested, clarified by low-speed centrifugation and added to wells of a 96-well plate. Purified FN, LN or TSP are added to each assay plate to serve as a standard. After 4-hour incubation, the culture medium from the cells, the control culture medium and the standards are removed from the wells and the ELISAs are preformed.

Ligand Binding Assay

In a standard binding assay, 2×105 keratinocytes in 24 well plates are washed twice with KBM. The cells are washed once with Earl's balanced salt solution (EBSS) containing 0.2% bovine serum albumin. The cells are chilled and then incubated with medium composed of EBSS with 0.2 bovine serum albumin (binding medium). After 6 hours the assay is terminated by washing the monolayers with cold binding medium, solubilization of cells in 0.1N sodium hydroxide containing 1% SDS and counting in a gamma counter. Non-specific binding was determined by adding an excess of unlabeled epidermal growth factor (EGF) to parallel samples well and was no greater than 5% of the total amount bound under any treatment condition.

The binding data are analyzed by a Scratchard plot.

Measure of Transforming Growth Factor-alpha Protein (TGF-alpha)

To determine the amount of TGF-alpha produced cultured keratinocytes, semiconfluent keratinocytes containing KGM are maintained for 48 hours at 37° C., and the conditioned medium is assayed for TGF-alpha using radio immunoassay kit. Duplicate aliquots are removed and immediately reduced and denatured. The samples are run with at least five different known TGF-alpha standards.

To determine the amount of TGF-alpha that may be bound to the keratinocyte cell surface, thoroughly washed keratinocytes are exposed to a cold acid wash in 50 mM glycine, 100 mM NaCl; pH 3.0 for 4 min at 4° C.

Measurement of TGF-alpha mRNA

Keratinocytes ($3 \times 10^6$) are lysed and RNA is isolated by centrifugation. RNA concentration is determined by absorbance at 260 nm and confirmed by nondenaturing agarose gel electro-phoresis. RNA are size-fractionated by electrophoresis on 1% formaldehyde-agarose gel and transferred to derivatized nylon membrane. Filters are hybridized against $^{32}P$ labeled probes prepared by random priming. Specific hybridization is estimated by subjecting the autoradiographs of the blots to laser scanning densitometry.

Example 18

Human Keratinocyte Growth Assay

Three separate experiments are designed to determine whether the compounds of the present invention would influence the growth of cultured human keratinocytes. The effects of all-trans-retinoic acid are established as a control. Each run utilizes a similar protocol. The procedure is as follows:

The 2nd passage adult human keratinocytes are seeded onto 35 mm plastic Petri dishes with $0.32 \times 10^6$ cells/plate present at the beginning of the experiment. After two days and change of the low calcium serum-free medium (keratinocyte growth medium, KGM-Clonetics Corp., San Diego, Calif.) containing EGF, insulin, and bovine pituitary extract, the cells are allowed to proliferate in the dark at 37° C. for an additional 3 days in the presence and absence of the 9-cis-retinoid of Example 1. The cell counts after three days are as follows (these cell counts are +/– a 10% standard error):

TABLE 6

| | Cells/Plate (duplicate dishes 4 separate counts pooled |
|---|---|
| KGM Alone | $1.98 \times 10^6$ |
| Retinoid Concentration (μg/ml) | |
| 0.01 | $2.63 \times 10^6$ |
| 0.05 | $2.10 \times 10^6$ |
| 0.10 | $1.64 \times 10^6$ |
| 0.50 | $1.49 \times 10^6$ |
| 1.0 | $1.36 \times 10^6$ |
| 5.0 | $0.72 \times 10^6$ |

The lowest concentration (0.01 and 0.05 g/ml) of the 9-cis-retinoid stimulates keratinocyte growth, whereas the higher concentration (0.5, 1.0 and 5.0 g/ml) inhibits growth. These dose-dependent pro-proliferative and anti-proliferative results are exactly the same as observed with all-trans-retinoic acid, except the present retinoid compound is more potent, as there is no growth promoting effects of all-trans-retinoic acid until 1.0 g/ml concentration is reached (approximately 100 times higher concentration).

There is no obvious effect on the differentiation of the keratinocytes.

Example 19

Topical Assay

A topical assay to test for pseudocomedone (utriculus) reduction in the rhino mouse is conducted.

Each test compound and a vehicle control was applied topically to the dorsal trunk of the rhino mouse. The utriculus diameters are measured with a ocular micrometer. The assay is based on the work of Kligman, et al. (1979) and Van Scott (1972). Kligman, et al., J. Invest. Derm., 73:354–358 (1979). Van Scott, Pharmacology of the Skin, eds. Montagna et al., New York, Appelton-Century-Crofts, 1972, pp. 523–533. Mann, Anat. Rec., 170:485–500 (1971). Mezick, et al, J. Invest. Derm., 83:110–113 (1984). Mezick et al., Models in Dermatology, eds. Maibach, et al., Basel, Karger, 1985.

The dorsal trunk of the rhino mouse is the test site. Each test compound is dissolved in alcohol:propylene glycol (70:30,v:v) or other suitable vehicle and topically applied (0.1 ml) to the dorsal trunk once daily, five consecutive days/week for two weeks. Following treatment, the animals are sacrificed by cervical dislocation. The treated dorsal trunk skin is removed from the animal and placed into 0.5% acetic acid for up to 18 hours at approximately 4° C. After this, the epidermis with the "acne cysts" is separated from the underlying dermis. The sheets of epidermis are processed by routine methods to permanent whole mounts for microscopic examination. Also, full-thickness samples are taken, stained (H&E) and examined by light microscope.

The utriculus diameters are measured with an ocular micrometer to compare effects of test compounds to vehicle control and/or reference compound on cyst reduction. Light microscopy is used to determine effects on cell differentiation. The results are summarized in Table 7.

TABLE 7

RHINO MOUSE UTRICULUS REDUCTION

| Retinoid | Dose (%) | Utriculus Reduction | $ED_{50}$ (%) | Relative Potency (95% Conf. Inter.) |
|---|---|---|---|---|
| all-trans-Retinoic Acid | 0.0005 | 34.1 | — | — |
| | 0.005 | 49.9 | 0.004 | 1 |
| | 0.05 | 72.8 | — | — |
| Example 1 | 0.0005 | 25.2 | — | — |
| | 0.005 | 45.7 | 0.01 | 0.4 (0.3, 0.5) |
| | 0.05 | — | 61.1 | — |

Example 20

The Draize Test for Irritation

The results of testing done on rabbits to determine dermal irritation are shown in Table 8.

TABLE 8

Rabbit Dermal Irritation

| Retinoid | Dose (%) | Erythema Grade | $ID_{50}$ (%) | Relative Potency (95% Conf. Inter.) |
|---|---|---|---|---|
| all-trans-Retinoic Acid | 0.001 | 0.4 | — | — |
| | 0.01 | 0.8 | 0.01 | 1 |
| | 0.1 | 2.8 | — | — |
| Example 1 | 0.001 | 0.0 | — | — |
| | 0.01 | 0.42 | 0.08 | 0.3 (0.1, 0.5) |
| | 0.1 | 1.75 | — | — |

The compound of Example 1 is 2.5 times less irritating than all-trans-RA in the rhino mouse and 3.3 times less irritating than all-trans-RA in rabbit dermal irritation.

Example 21–30

The Epithelial Wound Healing Model

Wounds that do not result in total skin loss but retain a portion of their dermis heal primarily by epidermal regeneration. It is known that tretinoin will accelerate skin healing but it is irritating and makes it unattractive for this use. In previous work molecular modification of isotretinoin observed the therapeutic benefits of isotretinoin without irritation. See Parish et al., U.S. Pat. Nos. 4,677,120 and 4,885,311. It was hypothesized that the new 9-cis-retinoids might retain the therapeutic benefit as wound healing chemicals without the associated irritation. Several of the 9-cis-retinoids were synthesized and evaluated using a battery of assays designed to measure the potential for epidermal regeneration and skin irritation. Ten 9-cis-retinoids were synthesized. Compounds were selected that have sufficient solubility in the vehicles commonly used for topical applications. Therefore, relatively low molecular weight derivatives were preferred. The 10 compounds selected for synthesis are shown in Examples 21–30.

Epithelial regeneration is the rate limiting factor in the healing of donor sites and partial thickness wounds. An increase in healing rate would allow donor sites to be reharvested more frequently and thus allow closure of the burn wound in a more timely fashion. In addition, the more rapid healing of partial thickness injuries would mean less pain for the patient and a more timely return to society as a functioning member. The objectives of this study are to:

1) study the rate of re-epithelization of a partial thickness injury in the pig model treated with topical tretinoin derivatives compared to control wounds, 2) develop a dose response determination for such a topical application,
3) review the healing process via histological examination.

The performance of this study requires pigs be used for a period of 14 days. The study lasts for 10 weeks using a total of 10 pigs. The pigs are anesthetized using 10 mg/kg ketamine and 2 mg/kg xylazine intramuscular injection. Lidocaine is used as a local subcutaneous injection. Rows of surgically created 2 cm×2 cm wounds are created on the dorsum of the animal. The wounds are formed using a Padgett electric dermatome (Padgett Company, Kansas City, Mo.) set at 0.016 inch. Each pig is used to test a different concentration of 9-cis-retinoids; and, different wounds are used to test varying numbers of applications per day, one acting as a control receiving no 9-cis-retinoid. The number of applications per day varies from once a day to four times a day. Kaltostat is used as a delivery mechanism.

The animals are anesthetized four times daily and appropriate 9-cis-retinoid applications are made to designated sites. Wound sites are covered by Compressor Grip® tubular elastic bandage #12 (36–48" circumference). Wound biopsies are taken from designated sites numbered 1 through 5 on each wound, chosen by a random method, on days 3, 5, 7, 9 and 12 for histological examination and comparison. Photographic documentation are obtained during the course of the study. After the 14 days of study, the pigs are anesthetized as usual and then euthanized using 0.14 ml/lb intravenous T61.

1) Each wound is a partial thickness wound created by a Padgett electric dermatome.
2) Each pig is used to test various numbers of applications per day on one concentration of topical 9-cis-retinoid.
Concentrations:
2 pigs-standardization of technique
2 pigs-2 mg/%
2 pigs-4 mg/%
2 pigs-8 mg/%
2 pigs-12 mg/%
3) Biopsies are taken for histological examination of wound sites to determine amount epithelial regeneration.
Row 1 is used as the biopsy site.
Biopsies are taken from randomly chosen biopsy sites numbered 1 through 5.
Biopsies are taken on 5 days of the study, on days 3, 5, 7, 9, 12. Biopsies do not contact the edge of the wound.
4) Visual healing is observed and recorded using photographic documentation with a digital camera, computer analysis and an analyst program.
5) Test rows receive topical 9-cis-retinoids.
6) Control rows do not receive topical 9-cis-retinoids.
7) Test sites are covered by Compressogrip tubular elastic bandage.

The results show an increase in the rate of wound healing of about 25 to about 30% for the 9-cis-retinoic acid esters and amides of the present invention, compared with untreated control sites, compared to about 15 to about 18% for all-trans-retinoic acid treated sites. Control sites on test animals showed an increase in wound healing rate of about 5% compared to untreated animals, indicating a slight systemic effect of the treatments.

Example 31

A mixture was formed of 2.42 g (27.89 mmol) of $MnO_2$, 0.35 g (7.2 mmol) of NaCN, 0.12 ml (2.1 mmol) glacial acetic acid in 20 ml of $CH_3OH$ at 0° C. A separate solution was formed of 600 mg (2.1 mmol) of 9-cis-retinal (I) in 9 ml of CH3OH, also at 0° C. The solution of 9-cis-retinal was added dropwise to the mixture and stirred for 2.5 h at constant temperature and the reaction mixture was filtered through Celite. The filter cake was washed with a 1:1 mixture of $CH_3OH$ and water. The filtrates were combined and diluted with additional water and then extracted three times with ether. The combined organic extracts were dried over $MgSO_4$ and concentrated under reduced pressure. Purification by silica gel flash column chromatography using 20:1 hexane:ethyl acetate as eluent gave the pure methyl ester of 9-cis-retinoic acid (II) in the amount of 530 mg, a yield of 80%. The structure was confirmed by NMR.

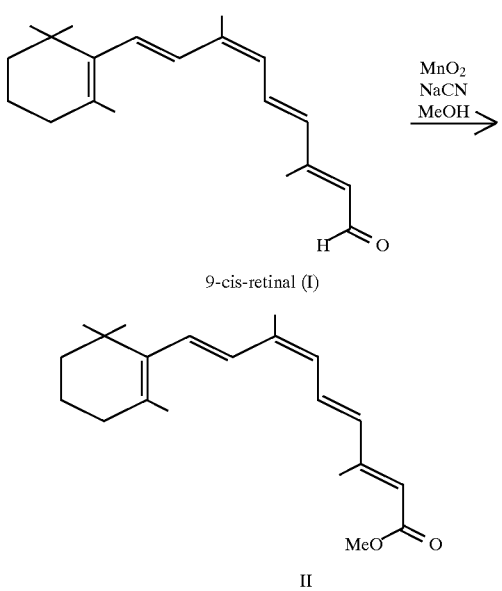

The methyl ester of 9-cis-retinoic acid (II), 530 mg, 1.68 mmol, was dissolved in 3 ml of THF, 8 ml CH3OH and 3 ml of water. A solution of 0.52 g (9.3 mmol) KOH in 8 ml $CH_3OH$ was added dropwise at ambient temperature and stirred for 24 hours. The bulk of the solvents, THF and $CH_3OH$, were removed under reduced pressure. The resulting aqueous phase was washed twice with ether and adjusted to pH 3 with 1N Hcl. The reaction product was extracted with ether (three times). The organic extracts were combined, dried over $MgSO_4$ and concentrated under reduced pressure to afford pure 9-cis-retinoic acid (III), 0.446 g, at a yield of 88%. The structure was confirmed by NMR.

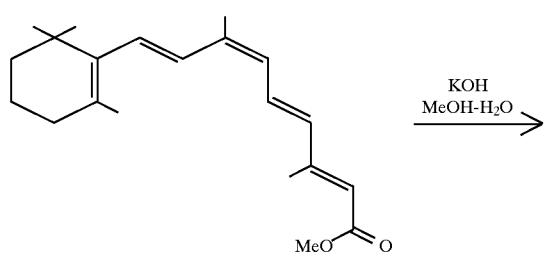

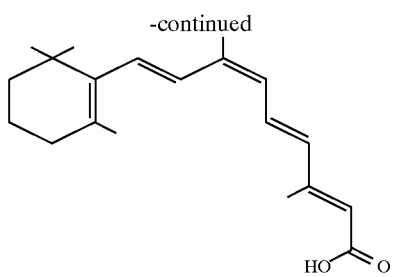

III

A solution of 0.450 g (1.50 mmol) of 9-cis-retinoic acid (III) was formed in 17 ml of DMF at 0° C. In sequence, 0.97 g (3.0 mmol) cesium carbonate and then 0.25 ml (1.9 mmol) 1-chloropinacolone were added to the solution. The reaction mixture was stirred at ambient temperature for 2 h, and the reaction was then quenched with the addition of 20 ml water. The reaction product was extracted with methylene chloride four times. The organic extracts were combined and dried over $MgSO_4$ and then concentrated under reduced pressure. Silica gel column purification using 5:1 hexane:ethyl acetate produced 480 g of product IV with a very small amount of 1-chloropinacolone. Repeated recrystallization with ethanol at low temperature gave 320 mg of pure IV, having a melting point of 81° C. The structure was confirmed by NMR.

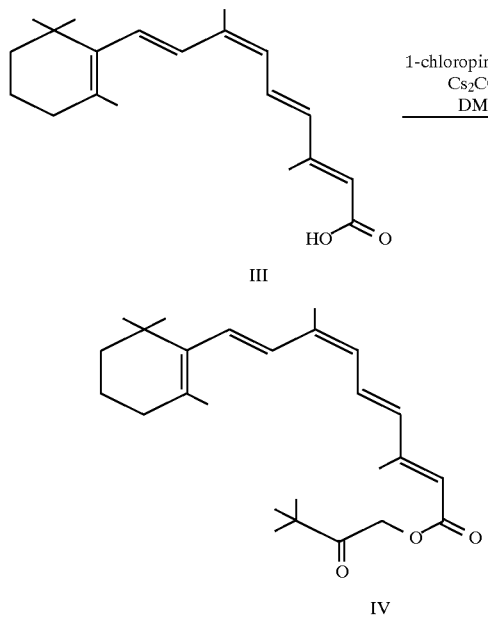

Human neonatal foreskin keratinocytes and human neonatal foreskin fibroblasts were isolated and grown in monlayer culture. Culture medium for keratinocytes was Keratincyte Growth Medium (KGM) from Clonetics, Inc., San Diego. Calif. The culture medium for fibroblasts was Dulbecco's Modified Eagle's Medium (DMEM) supplemented with non-essential amino acids and 10% fetal bovine serum. The culture medium was obtained from GIBCO, Grand Island, N.Y. and the FBS was from Hyclone Labs, Inc., Logan, Utah.

Cells at passage 2–4 were plated in wells of a 24 well dish at approximately $5\times10^4$ cells per well in their respective culture medium. Incubation was at 37° C. with $CO_2$. After the cells attached and spread overnight, they were washed two times in serum-free keratincyte basal medium (KBM) and incubated in 1 ml of KBM or in 1 ml of KGM. Compound IV was added in varying concentrations to the wells. All-trans-retinoic acid (or no treatment) was added to control wells. The cells were incubated for an additional two days for fibroblasts and three days for keratinocytes, and were then harvested and counted. The effect of IV and of the controls are shown for both cell types in Tables 9 and 10:

TABLE 9

HUMAN FIBROBLASTS

| Treatment | Concentration μg/ml | Number of Cells × $10^4$ |
|---|---|---|
| None | | 5.7 ± 0.6 |
| Retinoic Acid | 0.25 | 10.1 ± 0.2 |
| | 0.5 | 10.1 ± 0.1 |
| | 1.0 | 9.6 ± 0.1 |
| Compound IV | 0.1 | 6.4 ± 0.6 |
| | 0.25 | 5.8 ± 0.1 |
| | 0.5 | 5.5 ± 0.8 |
| | 1.0 | 7.9 ± 0.1 |
| | 5.0 | 8.5 ± 0.6 |
| | 10.0 | 7.5 ± 0.9 |

TABLE 10

Human Keratincytes

| | Concentration | Number of Cells × $10^4$ | |
|---|---|---|---|
| Treatment | μg/ml | KMB | KGM |
| None | | 8.4 ± 0.3 | 28.6 ± 3.4 |
| Retinoic Acid | 0.25 | 13.7 ± 1.6 | 24.7 ± 1.7 |
| | 0.5 | 15.2 ± 0.1 | 17.7 ± 0.8 |
| | 1.0 | 12.3 ± 1.0 | 10.9 ± 1.8 |
| Compound IV | 0.10 | 13.1 ± 0.5 | 27.4 ± 0.1 |
| | 0.25 | 13.1 ± 1.0 | 25.9 ± 0.4 |
| | 0.5 | 13.8 ± 2.4 | 22.5 ± 0.1 |
| | 1.0 | 14.0 ± 0.9 | 21.2 ± 0.8 |
| | 5.0 | 11.2 ± 1.2 | 6.4 ± 0.1 |
| | 10.0 | 8.4 ± 0.2 | 4.5 ± 0.2 |

Tables 9 and 10 demonstrate that Compound IV is effective to stimulate both fibroblast and keratinocyte viability and growth, but in a fashion more selective than retinoic acid. By comparison of the effects of retinoic acid and IV in these tests, it is possible to demonstrate that IV shows a potent "retinoid" effect on keratinocytes and a less active result with fibroblasts, consistent with the separation of the therapeutic activity from the well known and limiting side effects of retinoids.

I claim:

1. A compound selected from the group consisting of:

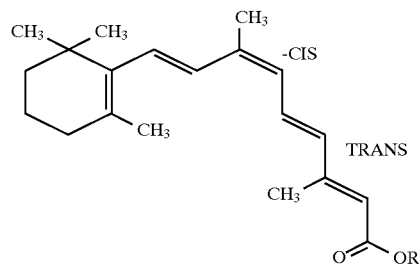

and

-continued

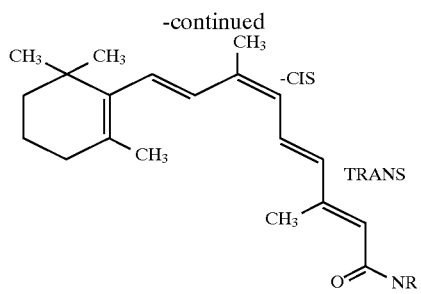

wherein R is

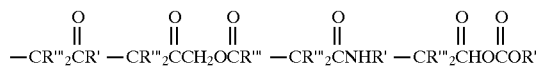

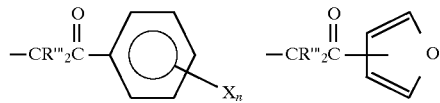

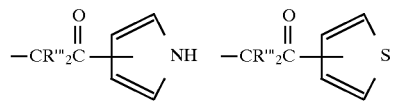

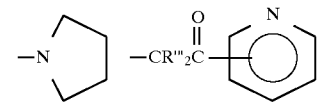

and

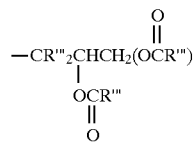

wherein X is $-H, -F, -Cl, -I, -OH,$

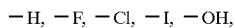

$-NO_2$ $-NH_2$, $-NHR'$, $-NR'_2$ and 

wherein n is a number from 1 to 5;
wherein R' is H or any of the lower alkyls ranging from $C_1$ to $C_6$;
wherein R" is

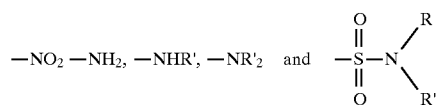

wherein R'" is R" or the hydrocarbon backbone of fatty acids;
wherein R"" is R" or the hydrocarbon backbone of fatty acids;

wherein R""' is the lower alkyls ranging from $C_1$ to $C_6$; and further, when there are two or more R', R", R'", R"", or R""' groups attached to the same carbon, each R", R", R'", R"", or R""' group may be the same as or different from the other R', R", R'", R"", or R""' groups attached to that carbon.

2. The compound of claim 1, having the formula:

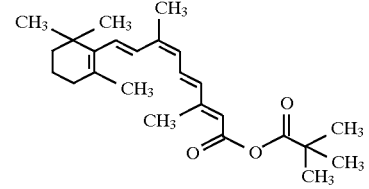

3. The compound of claim 1 wherein said compound is 1-(9-cis-retinoyloxy)-3-decanoyloxy-2-propanone.

4. The compound of claim 1 wherein said compound is 1,3-bis-(9-cis-retinoyloxy)-2-propanone.

5. The compound of claim 1 wherein said compound is 1-(9-cis-retinoyloxy)-2-pinacolone.

6. The compound of claim 1 wherein said compound is 2-(9-cis-retinoyloxy)-acetophenone.

7. The compound of claim 1 wherein said compound is 9-cis-retinoyloxy methyl 2,2-dimethyl propanoate.

8. The compound of claim 1 wherein said compound is 2-(9-cis-retinoyloxy)-n-methyl-acetamide.

9. The compound of claim 1 wherein said compound is 1-(9-cis-retinoyloxy)-3-hydroxy-2-propanone.

10. The compound of claim 1 wherein said compound is 1-(9-cis-retinoyloxy)-2,3-dioleoylpropanone.

11. The compound of claim 1 wherein said compound is succinimidyl 9-cis-retinoate.

12. A pharmaceutical composition for the treatment of the skin for a condition responsive to retinoids which comprises an effective amount of a 9-cis retinoid compound of the formula:

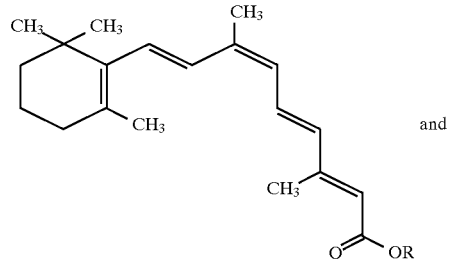

and

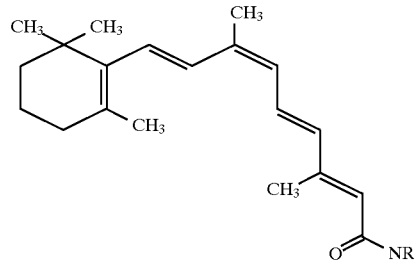

wherein R is

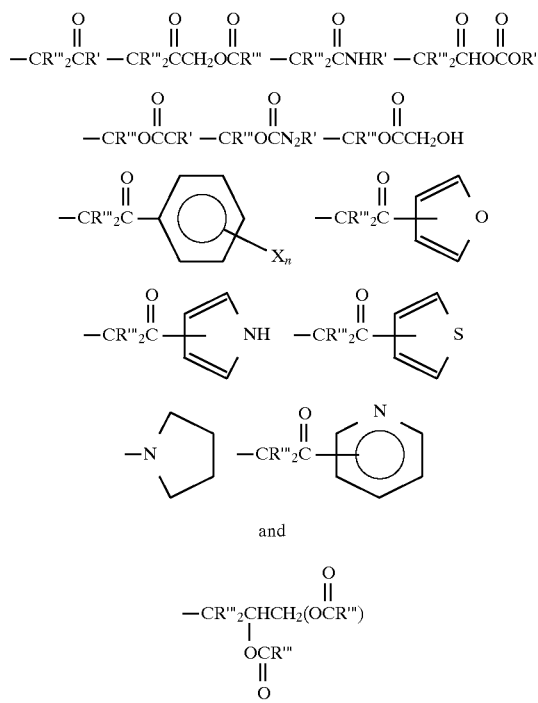

wherein X is

—H, —F, —Cl, —I, —OH,

—OR, —OR', —OCR', —CR'. —CH, —CN,

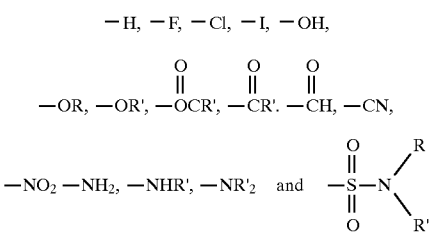

wherein n is a number from 1 to 5;
wherein R' is H or any of the lower alkyls ranging from $C_1$ to $C_6$;
wherein R" is

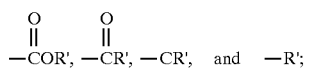

wherein R'" is R" or the hydrocarbon backbone of fatty acids;
wherein R"" is R" or the hydrocarbon backbone of fatty acids;
wherein R""' is the lower alkyls ranging from $C_1$ to $C_6$; and further,
when there are two or more R', R", R'", R"", or R""' groups attached to the same carbon, each R", R", R'", R"", or R""' group may be the same as or different from the other R', R", R'", R"", or R""' groups attached to that carbon,
admixed with a pharmaceutically acceptable vehicle.

13. The composition of claim 12, wherein said 9-cis-retinoid compound comprises from about 0.01% to about 0.05% by weight of said composition.

14. The composition of claim 12, wherein said 9-cis-retinoid compound comprises from about 0.05% to about 0.2% by weight of said composition.

15. The composition of claim 12, wherein said vehicle is a mixture selected from the group of propylene glycol-ethanol and propylene glycol-ethanol chloroform.

16. The composition of claim 12, having the formula:

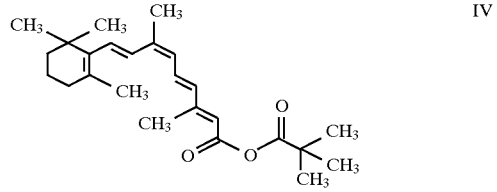

17. The composition of claim 12 wherein said compound is 1-(9-cis-retinoyloxy)-2-propanone.

18. The composition of claim 12 wherein said compound is 1-(9-cis-retinoyloxy)-3-decanoyloxy-2-propanone.

19. The composition of claim 12 wherein said compound is 1,3-bis-(9-cis-retinoyloxy)-2-propanone.

20. The composition of claim 12 wherein said compound is 1-(9-cis-retinoyloxy)-2-pincacolone.

21. The composition of claim 12 wherein said compound is 2-(9-cis-retinoyloxy)-acetophenone.

22. The composition of claim 12 wherein said compound is 9-cis-retinoyloxy methyl 2,2-dimethyl propanoate.

23. The composition of claim 12 wherein said compound is 2-(9-cis-retinoyloxy)-n-methyl-acetamide.

24. The composition of claim 12 wherein said compound is 1-(9-cis-retinoyloxy)-3-hydroxy-2-propanone.

25. The composition of claim 12 wherein said compound is 1-(9-cis-retinoyloxy)-2,3-dioleoylpropane.

26. The composition of claim 12 wherein said compound is succinimidyl 9-cis-retinoate.

27. A pharmaceutical composition for the treatment of wounds which comprises an effective growth stimulating amount of a wound treating compound of the formula:

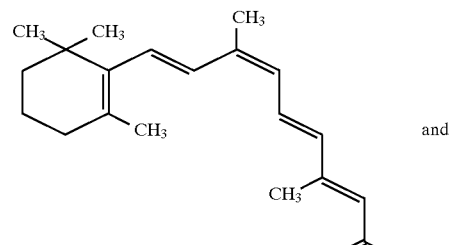

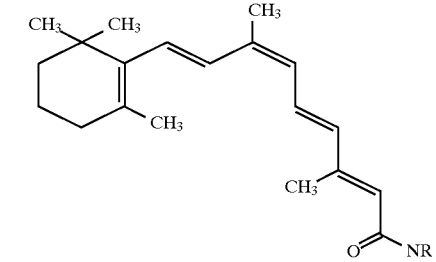

wherein R is

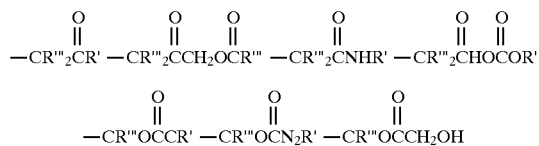

-continued

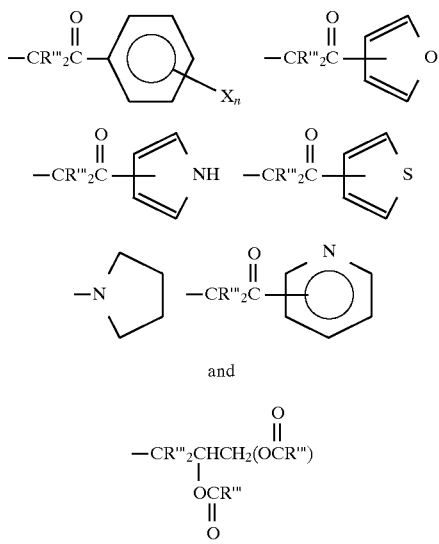

and

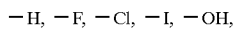

wherein X is

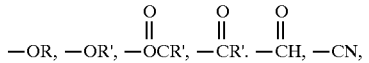

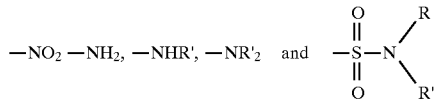

wherein n is a number from 1 to 5;
wherein R' is H or any of the lower alkyls ranging from $C_1$ to $C_6$;
wherein R" is

wherein R'" is R" or the hydrocarbon backbone of fatty acids;
wherein R"" is R" or the hydrocarbon backbone of fatty acids;

wherein R'"" is the lower alkyls ranging from $C_1$ to $C_6$; and further, when there are two or more R', R", R'", R"", or R'"" groups attached to the same carbon, each R", R", R'", R"", or R'"" group may be the same as or different from the other R', R", R'", R"", or R'"" groups attached to that carbon, admixed with a pharmaceutically acceptable carrier.

28. The pharmaceutical composition of claim 27 wherein said compound is 1-(9-cis-retinoyloxy)-2-propanone.

29. The pharmaceutical composition of claim 27 wherein said compound is 1-(9-cis-retinoyloxy)-3-decanoyloxy-2-propanone.

30. The pharmaceutical composition of claim 27 wherein said compound is 1,3-bis-(9-cis-retinoyloxy)-2-propanone.

31. The pharmaceutical composition of claim 27 wherein said compound is 1-(9-cis-retinoyloxy)-2-pinacolone.

32. The pharmaceutical composition of claim 27 wherein said compound is 2-(9-cis-retinoyloxy)-acetophenone.

33. The pharmaceutical composition of claim 27 wherein said compound is 9-cis-retinoyloxy methyl 2,2-dimethyl propanoate.

34. The pharmaceutical composition of claim 27 wherein said compound is 2-(9-cis-retinoyloxy)-n-methyl-acetamide.

35. The pharmaceutical composition of claim 27 wherein said compound is 1-(9-cis-retinoyloxy)-3-hydroxy-2-propanone.

36. The pharmaceutical composition of claim 27 wherein said compound is 1-(9-cis-retinoyloxy)-2,3-dioleoylpropanone.

37. The pharmaceutical composition of claim 27 wherein said compound is succinimidyl 9-cis-retinoate.

38. The pharmaceutical composition of claim 27 wherein said wound-healing compound comprises from about 0.005% to about 0.1% by weight of said composition.

39. The pharmaceutical composition of claim 27, wherein said wound-healing compound comprises from about 0.01% to about 0.05% by weight of said composition.

40. The pharmaceutical composition of claim 27, wherein said vehicle is a mixture selected from the group consisting of propylene glycol-ethanol and propylene glycol-ethanol chloroform.

* * * * *